(12) United States Patent
Alberti et al.

(10) Patent No.: US 7,459,454 B2
(45) Date of Patent: Dec. 2, 2008

(54) AMINOPYRAZINE DERIVATIVES AND COMPOSITIONS

(75) Inventors: Michael John Alberti, Durham, NC (US); David Harold Drewry, Durham, NC (US); David Drysdale Miller, Stevenage (GB); Paul Bamborough, Stevenage (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 483 days.

(21) Appl. No.: 10/549,972

(22) PCT Filed: Mar. 18, 2004

(86) PCT No.: PCT/US2004/008301

§ 371 (c)(1),
(2), (4) Date: Sep. 20, 2005

(87) PCT Pub. No.: WO2004/084813

PCT Pub. Date: Oct. 7, 2004

(65) Prior Publication Data

US 2006/0084651 A1 Apr. 20, 2006

Related U.S. Application Data

(60) Provisional application No. 60/456,872, filed on Mar. 21, 2003.

(51) Int. Cl.
| | |
|---|---|
| *A01N 43/58* | (2006.01) |
| *A01N 43/60* | (2006.01) |
| *A61K 31/50* | (2006.01) |
| *A61K 31/495* | (2006.01) |
| *A61K 31/4965* | (2006.01) |
| *C07D 487/00* | (2006.01) |
| *C07D 473/00* | (2006.01) |
| *C07D 239/02* | (2006.01) |
| *C07D 401/00* | (2006.01) |
| *C07D 403/00* | (2006.01) |
| *C07D 405/00* | (2006.01) |
| *C07D 409/00* | (2006.01) |
| *C07D 411/00* | (2006.01) |
| *C07D 413/00* | (2006.01) |
| *C07D 417/00* | (2006.01) |
| *C07D 419/00* | (2006.01) |

(52) U.S. Cl. .......... 514/248; 514/249; 514/255.05; 544/236; 544/277; 544/330; 544/405

(58) Field of Classification Search .......... 514/248
See application file for complete search history.

(56) References Cited

FOREIGN PATENT DOCUMENTS

| | | | |
|---|---|---|---|
| WO | 2002060492 A1 | | 8/2002 |
| WO | 03/066629 | | 8/2003 |
| WO | WO 03/066629 | * | 8/2003 |

OTHER PUBLICATIONS

U.S. Appl. No. 10/481,699, filed Dec. 22, 2003, Berg et al.
U.S. Appl. No. 10/508,592, filed Sep. 22, 2004, Alberti et al.
U.S. Appl. No. 10/508,760, filed Sep. 22, 2004, Bailey et al.

* cited by examiner

*Primary Examiner*—James O. Wilson
*Assistant Examiner*—Jeffrey H Murray
(74) *Attorney, Agent, or Firm*—Kathryn L. Coulter; John L. Lemanowicz

(57) ABSTRACT

The present invention relates to aminopyrazine derivatives, compositions and medicaments containing the same, as well as processes for the preparation and use of such compounds, compositions and medcicaments. Such aminopyrazine derivatives are useful in the treatment of diseases associated with inappropriate tyrosine and/or serine/threonine kinase activity.

4 Claims, No Drawings

US 7,459,454 B2

AMINOPYRAZINE DERIVATIVES AND COMPOSITIONS

CROSS-REFERENCE TO RELATED APPLICATIONS

This application is filed pursuant to 35 U.S.C. § 371 as a United States National Phase Application of International Application No. PCT/US2004/008301 filed Mar. 18, 2004, which claims the benefit of U.S. Provisional Application No. 60/456,872, filed Mar. 21, 2003.

FIELD OF THE INVENTION

The present invention relates to aminopyrazine derivatives, compositions and medicaments containing the same, as well as processes for the preparation and use of such compounds, compositions and medicaments. Such aminopyrazine derivatives are useful in the treatment of diseases associated with inappropriate tyrosine and/or serine/threonine kinase activity.

BACKGROUND OF THE INVENTION

An important large family of enzymes is the protein kinase enzyme family. Currently, there are about 400 different known protein kinases. However, because three to four percent of the human genome is a code for the formation of protein kinases, there may be many thousands of distinct and separate kinases in the human body. Protein kinases serve to catalyze the phosphorylation of an amino acid side chain in various proteins by the transfer of the γ-phosphate of the $ATP\text{-}Mg^{2+}$ complex to said amino acid side chain. These enzymes control the majority of the signaling processes inside cells, thereby governing cell function, growth, differentiation and destruction (apoptosis) through reversible phosphorylation of the hydroxyl groups of serine, threonine and tyrosine residues in proteins. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity. Due to their physiological relevance, variety and ubiquitousness, protein kinases have become one of the most important and widely studied family of enzymes in biochemical and medical research.

The protein kinase family of enzymes is typically classified into two main subfamilies: Protein Tyrosine Kinases and Protein Serine/Threonine Kinases, based on the amino acid residue they phosphorylate. The serine/threonine kinases (PSTK), includes cyclic AMP- and cyclic GMP-dependent protein kinases, calcium- and phospholipid-dependent protein kinase, calcium- and calmodulin-dependent protein kinases, casein kinases, cell division cycle protein kinases and others. These kinases are usually cytoplasmic or associated with the particulate fractions of cells, possibly by anchoring proteins. Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are important targets for drug design. The tyrosine kinases phosphorylate tyrosine residues. Tyrosine kinases play an equally important role in cell regulation. These kinases include several receptors for molecules such as growth factors and hormones, including epidermal growth factor receptor, insulin receptor, platelet derived growth factor receptor and others. Studies have indicated that many tyrosine kinases are transmembrane proteins with their receptor domains located on the outside of the cell and their kinase domains on the inside. Much work is also under progress to identify modulators of tyrosine kinases as well.

A major signal transduction systems utilized by cells is the RhoA-signalling pathways. RhoA is a small GTP binding protein that can be activated by several extracellular stimuli such as growth factor, hormones, mechanic stress, osmotic change as well as high concentration of metabolite like glucose. RhoA activation involves GTP binding, conformation alteration, post-translational modification (geranylgeranyllization and farnesylation) and activation of its intrinsic GTPase activity. Activated RhoA is capable of interacting with several effector proteins including ROCKs and transmit signals into cellular cytoplasm and nucleus.

ROCK1 and 2 constitute a family of kinases that can be activated by RhoA-GTP complex via physical association. Activated ROCKs phosphorylate a number of substrates and play important roles in pivotal cellular functions. The substrates for ROCKs include myosin binding subunit of myosin light chain phosphatase (MBS, also named MYPT1), adducin, moesin, myosin light chain (MLC), LIM kinase as well as transcription factor FHL. The phosphorylation of theses substrates modulate the biological activity of the proteins and thus provide a means to alter cell's response to external stimuli. One well documented example is the participation of ROCK in smooth muscle contraction. Upon stimulation by phenylephrine, smooth muscle from blood vessels contracts. Studies have shown that phenylephrine stimulates b-adrenergic receptors and leads to the activation of RhoA. Activated RhoA in turn stimulates kinase activity of ROCK1 and which in turn phosphorylates MBS. Such phosphorylation inhibits the enzyme activity of myosin light chain phosphatase and increases the phosphorylation of myosin light chain itself by a calcium-dependent myosin light chain kinase (MLCK) and consequently increases the contractility of myosin-actin bundle, leading to smooth muscle contraction. This phenomena is also sometimes called calcium sensitization. In addition to smooth muscle contraction, ROCKs have also been shown to be involved in cellular functions including apoptosis, cell migration, transcriptional activation, fibrosis, cytokinesis, inflammation and cell proliferation. Moreover, in neurons ROCK plays a critical role in the inhibition of axonal growth by myelin-associated inhibitory factors such as myelin-associated glycoprotein (MAG). ROCK-activity also mediates the collapse of growth cones in developing neurons. Both processes are thought to be mediated by ROCK-induced phosphorylation of substrates such as LIM kinase and myosin light chain phosphatase, resulting in increased contractility of the neuronal actin-myosin system.

Inhibitors of ROCKs have been suggested for use in the treatments of a variety of diseases. They include cardiovascular diseases such as hypertension, chronic and congestive heart failure, cardiac hypertrophy, restenosis, chronic renal failure and atherosclerosis. In addition, because of its muscle relaxing properties, it is also suitable for asthma, male erectile dysfunctions, female sexual dysfunction and over-active bladder syndrome. ROCK inhibitors have been shown to possess anti-inflammatory properties. Thus they can be used as treatment for neuroinflammatory diseases such as stroke, multiple sclerosis, Alzheimer's disease, Parkinson's disease, amyotrophic lateral sclerosis and inflammatory pain, as well as other inflammatory diseases such as rheumatoid arthritis, irritable bowel syndrome, inflammatory bowel disease. In addition, based on their neurite outgrowth inducing effects, ROCK inhibitors could be useful drugs for neuronal regeneration, inducing new axonal growth and axonal rewiring across lesions within the CNS. ROCK inhibitors are therefore likely to be useful for regenerative (recovery) treatment of CNS disorders such as spinal cord injury, acute neuronal injury (stroke, traumatic brain injury), Parkinsons disease, Alzheimers disease and other neurodegenerative disorders. Since ROCK inhibitors reduce cell proliferation and cell migration, they could be useful in treating cancer and tumor metastasis. Further more, there is evidence suggesting that ROCK inhibitors suppress cytoskeletal rearrangement upon virus invasion, thus they also have potential therapeutic value in anti-viral and anti-bacterial applications. ROCK inhibitors are also useful for the treatment of insulin resistance and diabetes.

The present inventors have discovered novel amino-pyrazine compounds, which are inhibitors of ROCK activity. Such derivatives are useful in the treatment of disorders associated with inappropriate ROCK activity.

SUMMARY OF THE INVENTION

In one aspect of the present invention, there is provided a compound of Formula (I):

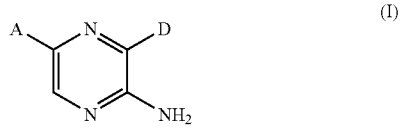

or a salt, solvate, or physiologically functional derivative thereof:

wherein:

A is aryl, heteroaryl, $C_1$-$C_6$ alkenyl, $C_1$-$C_6$ alkynyl, —CN, halo, —COOH, —C(O)NR$^4$R$^5$, —NRR', —N(R')S(O)$_2$R, —N(R')C(O)R, or —N(R')C(O)NR$^4$R$^5$;

R is —H, $C_1$-$C_6$ alkyl, aryl, or heteroaryl;

R' is —H or $C_1$-$C_3$ alkyl;

D is selected from the group:

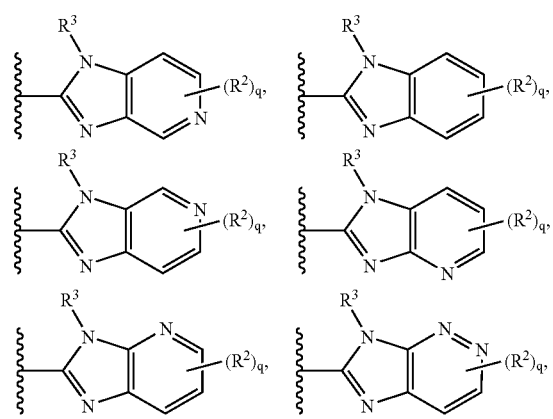

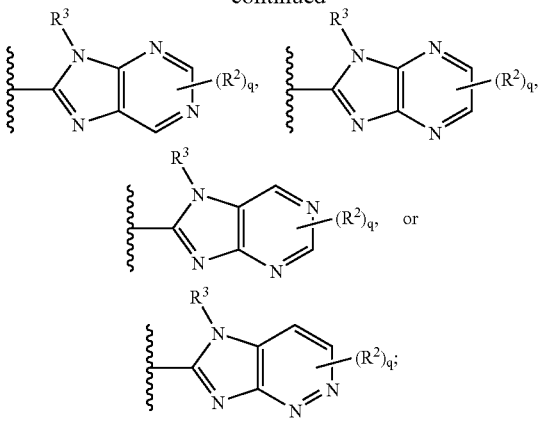

$R^2$ is —H, halo, $C_1$-$C_6$ alkyl, $C_1$-$C_6$ alkoxy, aryl, heteroaryl, —S(O)$_2$NR$^4$R$^5$, —COOH, —C(O)OR$^6$, —C(O)NR$^4$R$^5$, NRR', —N(H)C(O)NRR', —N(H)C(O)R, or —N(H)S(O)$_2$R;

q is 1, 2, 3, or 4;

$R^3$ is —H, $C_1$-$C_3$ alkyl, aryl, aralkyl, or heteroaryl;

$R^4$ is —H or $C_1$-$C_3$ alkyl;

$R^5$ is —H or $C_1$-$C_3$ alkyl; or $R^4$ and $R^5$ together with the nitrogen to which they are attached form a heterocyclyl ring, said ring optionally containing 1 or 2 additional oxygen, S(O)$_m$, or nitrogen atoms; said nitrogen atoms being optionally substituted by a $C_1$-$C_3$ alkyl group;

m is 0, 1, or 2; and $R^6$ is $C_1$-$C_6$ alkyl.

In a second aspect of the present invention, there is provided a compound of Formula (I):

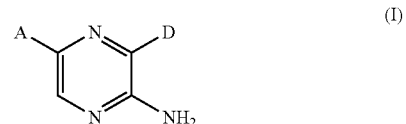

or a salt, solvate, or physiologically functional derivative thereof:

wherein:

A is aryl optionally substituted with at least one $R^1$ group, heteroaryl optionally substituted with at least one $R^1$ group, $C_1$-$C_6$ alkenyl, $C_1$-$C_6$ alkynyl, —CN, halo, —COOH, —C(O)NR$^4$R$^5$, —NRR', —N(R')S(O)$_2$R, —N(R')C(O)R, or —N(R')C(O)NR$^4$R$^5$;

R is —H, $C_1$-$C_6$ alkyl, aryl, or heteroaryl;

R' is —H or $C_1$-$C_3$ alkyl;

$R^1$ is $C_1$-$C_6$ alkyl, aryl, $C_1$-$C_6$ alkoxy, aryloxy, halo, —COOH, —CN, —S(O)$_2$NR$^4$R$^5$, —S(O)$_2$R, —C(O)NR$^4$R$^5$, —NRR', —N(H)C(O)NR$^4$R$^5$, —O(CH$_2$)$_n$COOH, —(CH$_2$)$_n$COOH, —C(O)O(CH$_2$)$_n$R, —(CH$_2$)$_n$N(H)C(O)OR, or —N(R')S(O)$_2$R;

n is 1, 2, 3, or 4;

D is selected from the group:

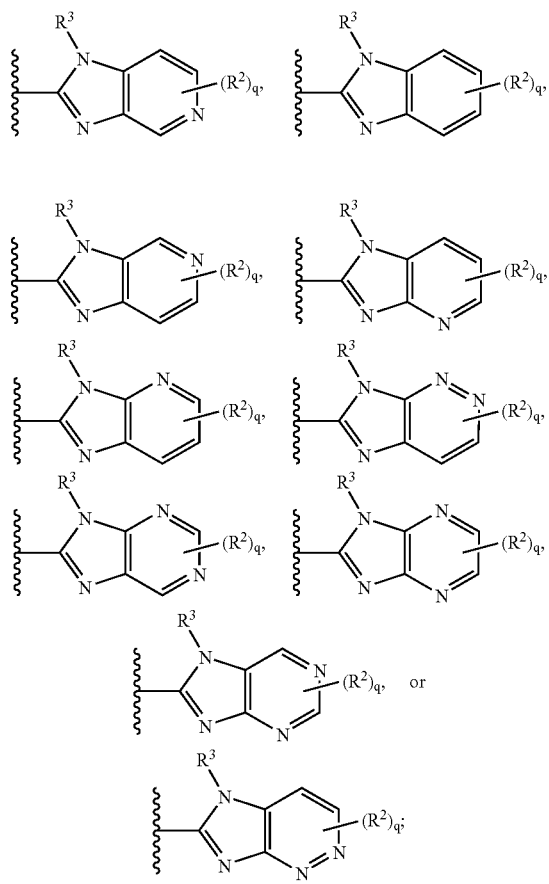

R² is —H, halo, C₁-C₆ alkyl, C₁-C₆ alkoxy, heteroaryl, —S(O)₂NR⁴R⁵, —COOH, —C(O)OR⁶N or —C(O)NR⁴R⁵, NRR', —N(H)C(O)NRR', —N(H)C(O)R, or —N(H)S(O)₂R;

q is 1, 2, 3, or 4;

R³ is —H, C₁-C₃ alkyl, aryl, aralkyl, or heteroaryl;

R⁴ is —H or C₁-C₃ alkyl;

R⁵ is —H or C₁-C₃ alkyl; or

R⁴ and R⁵ together with the nitrogen to which they are attached form a heterocyclyl ring, said ring optionally containing 1 or 2 additional oxygen, S(O)ₘ, or nitrogen atoms; said nitrogen atoms being optionally substituted by a C₁-C₃ alkyl group;

m is 0, 1, or 2; and

R⁶ is C₁-C₆ alkyl.

In third aspect of the present invention, there is provided a compound of Formula (I):

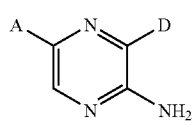

(I)

or a salt, solvate, or physiologically functional derivative thereof:

wherein:

A is aryl optionally substituted with at least one R¹ group or heteroaryl optionally substituted with at least one R¹ group;

R is —H, C₁-C₆ alkyl, aryl, or heteroaryl;

R' is —H or C₁-C₃ alkyl;

R¹ is C₁-C₆ alkyl, aryl, C₁-C₆ alkoxy, aryloxy, halo, —COOH, —CN, —S(O)₂NR⁴R⁵, —S(O)₂R, —C(O)NR⁴R⁵, —NRR', —N(H)C(O)NR⁴R⁵, —O(CH₂)ₙCOOH, —(CH₂)ₙCOOH, —C(O)O(CH₂)ₙR, —(CH₂)ₙN(H)C(O)OR, or —N(R')S(O)₂R;

D is selected from the group:

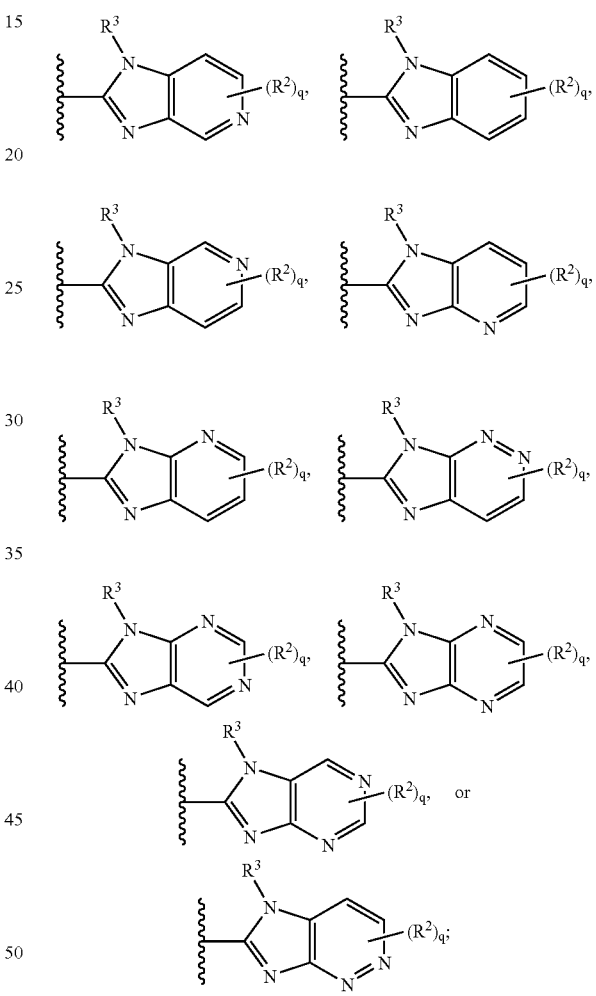

R² is —H, halo, C₁-C₆ alkyl, C₁-C₆ alkoxy, heteroaryl, —S(O)₂NR⁴R⁵, —COOH, —C(O)OR⁶, or —C(O)NR⁴R⁵, NRR', —N(H)C(O)NRR', —N(H)C(O)R, or —N(H)S(O)₂R;

q is 1, 2, 3, or 4;

R³ is —H, C₁-C₃ alkyl, aryl, aralkyl, or heteroaryl;

R⁴ is —H or C₁-C₃ alkyl;

R⁵ is —H or C₁-C₃ alkyl; or

R⁴ and R⁵ together with the nitrogen to which they are attached form a heterocyclyl ring, said ring optionally containing 1 or 2 additional oxygen, S(O)ₘ, or nitrogen atoms; said nitrogen atoms being optionally substituted by a C₁-C₃ alkyl group;

m is 0, 1, or 2; and $R^6$ is $C_1$-$C_6$ alkyl.

In a fourth aspect of the present invention, there is provided a compound of Formula (I):

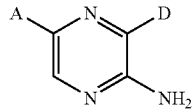
(I)

or a salt, solvate, or physiologically functional derivative thereof:

wherein:
A is $C_1$-$C_6$ alkenyl or $C_1$-$C_6$ alkynyl;
R is —H, $C_1$-$C_6$ alkyl, aryl, or heteroaryl;
R' is —H or $C_1$-$C_3$ alkyl;
D is selected from the group:

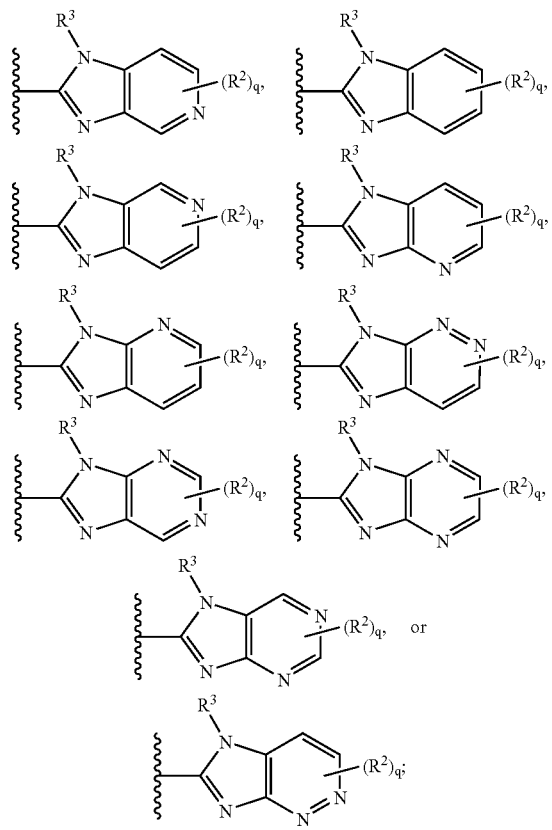

$R^2$ is —H, halo, $C_1$-$C_6$ alkyl, $C_1$-$C_6$ alkoxy, heteroaryl, —S(O)$_2$NR$^4$R$^5$, —COOH, —C(O)OR$^6$, or —C(O)NR$^4$R$^5$, NRR', —N(H)C(O)NRR', —N(H)C(O)R, or —N(H)S(O)$_2$R;
q is 1, 2, 3, or 4;
$R^3$ is —H, $C_1$-$C_3$ alkyl, aryl, aralkyl, or heteroaryl;
$R^4$ is —H or $C_1$-$C_3$ alkyl;
$R^5$ is —H or $C_1$-$C_3$ alkyl; or
$R^4$ and $R^5$ together with the nitrogen to which they are attached form a heterocyclyl ring, said ring optionally containing 1 or 2 additional oxygen, S(O)$_m$, or nitrogen atoms; said nitrogen atoms being optionally substituted by a $C_1$-$C_3$ alkyl group;

m is 0, 1, or 2; and
$R^6$ is $C_1$-$C_6$ alkyl.

In a fifth aspect of the present invention, there is provided a compound of Formula (I):

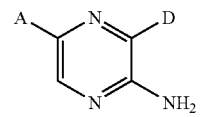
(I)

or a salt, solvate, or physiologically functional derivative thereof:

wherein:
A is —CN, —COOH, or —C(O)NR$^4$R$^5$;
R is —H, $C_1$-$C_6$ alkyl, aryl, or heteroaryl;
R' is —H or $C_1$-$C_3$ alkyl;
D is selected from the group:

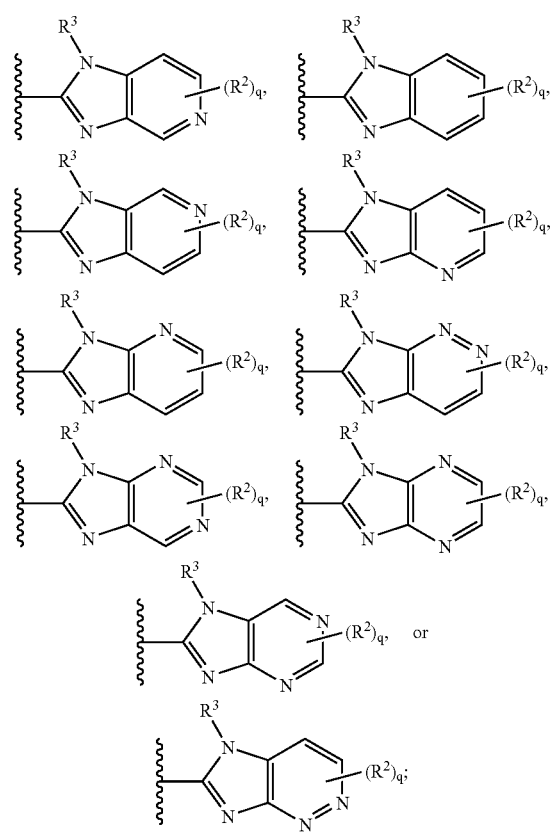

$R^2$ is —H, halo, $C_1$-$C_6$ alkyl, —COOH, $C_1$-$C_6$ alkoxy, heteroaryl, —S(O)$_2$NR$^4$R$^5$, —C(O)OR$^6$, or —C(O)NR$^4$R$^5$, NRR', —N(H)C(O)NRR', —N(H)C(O)R, or —N(H)S(O)$_2$R;
q is 1, 2, 3, or 4;
$R^3$ is —H, $C_1$-$C_3$ alkyl, aryl, aralkyl, or heteroaryl;
$R^4$ is —H or $C_1$-$C_3$ alkyl;
$R^5$ is —H or $C_1$-$C_3$ alkyl; or
$R^4$ and $R^5$ together with the nitrogen to which they are attached form a heterocyclyl ring, said ring optionally containing 1 or 2 additional oxygen, $S(O)_m$, or nitrogen atoms; said nitrogen atoms being optionally substituted by a $C_1$-$C_3$ alkyl group;

m is 0, 1, or 2; and $R^6$ is $C_1$-$C_6$ alkyl.

In a sixth aspect of the present invention, there is provided a compound of Formula (I):

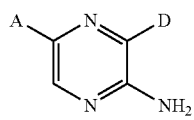

or a salt, solvate, or physiologically functional derivative thereof:

wherein:

A is —NRR', —N(R')S(O)$_2$R, —N(R')C(O)R, or —N(R')C(O)NR$^4$R$^5$;

R is —H, $C_1$-$C_6$ alkyl, aryl, or heteroaryl;

R' is —H or $C_1$-$C_3$ alkyl;

D is selected from the group:

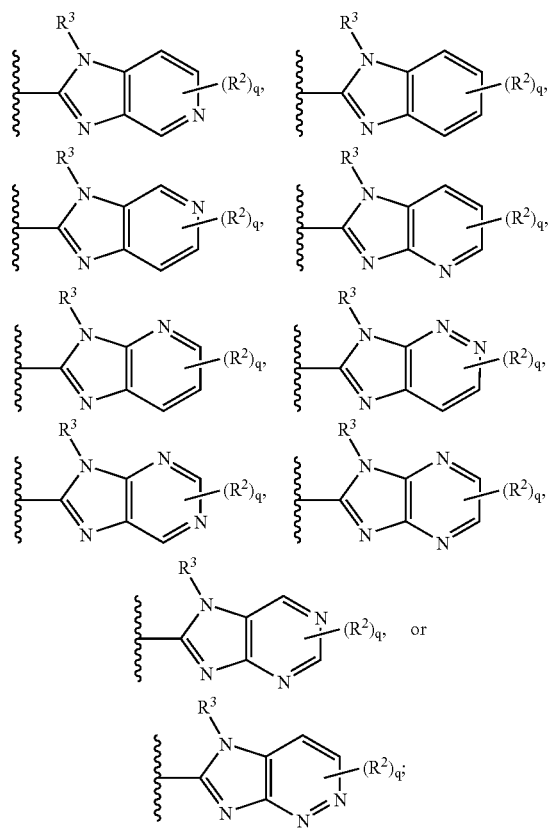

$R^2$ is —H, halo, $C_1$-$C_6$ alkyl, $C_1$-$C_6$ alkoxy, heteroaryl, —S(O)$_2$NR$^4$R$^5$, —COOH, —C(O)OR$^6$, or —C(O)NR$^4$R$^5$, NRR', —N(H)C(O)NRR', —N(H)C(O)R, or —N(H)S(O)$_2$R;

q is 1, 2, 3, or 4;

$R^3$ is —H, $C_1$-$C_3$ alkyl, aryl, aralkyl, or heteroaryl;

$R^4$ is —H or $C_1$-$C_3$ alkyl;

$R^5$ is —H or $C_1$-$C_3$ alkyl; or $R^4$ and $R^5$ together with the nitrogen to which they are attached form a heterocyclyl ring, said ring optionally containing 1 or 2 additional oxygen, $S(O)_m$, or nitrogen atoms; said nitrogen atoms being optionally substituted by a $C_1$-$C_3$ alkyl group;

m is 0, 1, or 2; and $R^5$ is $C_1$-$C_6$ alkyl.

In a seventh aspect of the present invention, there is provided a pharmaceutical composition comprising a therapeutically effective amount of a compound of formula (I) or a salt, solvate, or a physiologically functional derivative thereof and one or more of pharmaceutically acceptable carriers, diluents and excipients.

In an eighth aspect of the present invention, there is provided a method of treating a disorder in a mammal, said disorder being mediated by inappropriate ROCK-1 activity, comprising: administering to said mammal a therapeutically effective amount of a compound of formula (I) or a salt, solvate or a physiologically functional derivative thereof.

In a ninth aspect of the present invention, there is provided a compound of formula (I), or a salt, solvate, or a physiologically functional derivative thereof for use in therapy.

In a tenth aspect of the present invention, there is provided the use of a compound of formula (I), or a salt, solvate, or a physiologically functional derivative thereof in the preparation of a medicament for use in the treatment of a disorder mediated by inappropriate ROCK-1 activity.

DETAILED DESCRIPTION OF THE INVENTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "alkyl" refers to a straight- or branched-chain hydrocarbon radical having from one to twelve carbon atoms, optionally substituted with substituents selected from the group consisting of $C_1$-$C_6$ alkyl, $C_1$-$C_6$ hydroxyalkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aryl, aryloxy, heteroaryl, heterocyclyl, aminosulfonyl optionally substituted by alkyl, nitro, cyano, halo, or $C_1$-$C_6$ perfluoroalkyl, multiple degrees of substitution being allowed. Examples of "allkyl" as used herein include, but are not limited to, methyl, ethyl, n-propyl, isopropyl, n-butyl, isobutyl, t-butyl, n-pentyl, isopentyl, and the like.

As used herein, the terms "$C_1$-$C_3$ alkyl" and "$C_1$-$C_6$ alkyl" refer to an alkyl group, as defined above, containing at least 1, and at most 3 or 6 carbon atoms respectively. Examples of such branched or straight-chained alkyl groups useful in the present invention include, but are not limited to, methyl, ethyl, n-propyl, isopropyl, isobutyl, n-butyl, t-butyl, n-pentyl, isopentyl, and n-hexyl.

As used herein, the term "alkylene" refers to a straight or branched chain divalent hydrocarbon radical having from one to ten carbon atoms, optionally substituted with substituents selected from the group which includes $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aryl, heteroaryl, heterocyclyl, aminosulfonyl optionally substituted by alkyl, nitro, cyano, halo, and $C_1$-$C_6$ perfluoroalkyl, multiple degrees of substitution being allowed. Examples of "alkylene" as used herein include, but are not limited to, methylene, ethylene, n-propylene, n-butylene, and the like.

As used herein, the term "$C_1$-$C_3$ alkylene" refers to an alkylene group, as defined above, which contains at least 1, and at most 3 or 6, carbon atoms respectively. Examples of "$C_1$-$C_6$ alkylene" and "$C_1$-$C_6$ alkylene" groups useful in the present invention include, but are not limited to, methylene, ethylene, n-propylene, n-butylene, isopentylene, and the like.

As used herein, the term "halogen" refers to fluorine (F), chlorine (Cl), bromine (Br), or iodine (I) and the term "halo" refers to the halogen radicals: fluoro (—F), chloro (—Cl), bromo (—Br), and iodo (—I).

As used herein, the term "$C_1$-$C_6$ haloalkyl" refers to an alkyl group as defined above containing at least 1, and at most 6 carbon atoms respectively substituted with at least one halo group, halo being as defined herein. Examples of such branched or straight chained haloalkyl groups useful in the present invention include, but are not limited to, methyl, ethyl, propyl, isopropyl, isobutyl and n-butyl substituted independently with one or more halos, e.g., fluoro, chloro, bromo and iodo.

As used herein, the term "cycloalkyl" refers to a non-aromatic cyclic hydrocarbon ring containing from 3 to 10 carbon atoms and which optionally includes a $C_1$-$C_6$ alkyl linker through which it may be attached. In a like manner the term "$C_3$-$C_7$ cycloalkyl" refers to a non-aromatic cyclic hydrocarbon ring having from three to seven carbon atoms and which optionally includes a $C_1$-$C_6$ alkyl linker through which it may be attached. The $C_1$-$C_6$ alkyl group is as defined above. Exemplary "$C_3$-$C_7$ cycloalkyl" groups useful in the present invention include, but are not limited to, cyclopropyl, cyclobutyl, cyclopentyl, cyclohexyl and cycloheptyl.

As used herein, the term "heterocyclic" or the term "heterocyclyl" refers to a three to twelve-membered non-aromatic heterocyclic ring, being saturated or having one or more degrees of unsaturation, containing one or more heteroatom substitutions selected from S, S(O), S(O)$_2$, O, or N, optionally substituted with substituents selected from the group consisting of $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halo, aryl, aralkyl, heteroaryl, or $C_1$-$C_6$ perfluoroalkyl, multiple degrees of substitution being allowed. Such a ring may be optionally fused to one or more other "heterocyclic" ring(s) or cycloalkyl ring(s). Examples of "heterocyclic" moieties include, but are not limited to, tetrahydrofuran, pyran, 1,4-dioxane, 1,3-dioxane, piperidine, piperazine, 2,4-piperazinedione, pyrrolidine, imidazolidine, pyrazolidine, morpholine, thiomorpholine, tetrahydrothiopyran, tetrahydrothiophene, and the like.

As used herein, the term "aryl" refers to an optionally substituted benzene ring or to an optionally substituted benzene ring system fused to one or more optionally substituted benzene rings to form, for example, anthracene, phenanthrene, or napthalene ring systems. Exemplary optional substituents include $C_1$-$C_6$ alkyl, $C_1$-$C_6$ alkoxy, $C_1$-$C_6$ haloalkyl, $C_1$-$C_6$ haloalkoxy, $C_1$-$C_6$ alkylsulfanyl, $C_1$-$C_6$ alkylsulfenyl, $C_1$-$C_6$ alkylsulfonyl, $C_1$-$C_6$ alkylsulfonylamino, arylsulfonoamino, alkylcarboxy, alkylcarboxyamide, oxo, hydroxy, mercapto, amino optionally substituted by alkyl, aryl, or heteroaryl, carboxy, tetrazolyl, carboxamide, carbamoyl optionally substituted by alkyl, aryl, or heteroaryl, aminosulfonyl, acyl, aroyl, aroylamino, heteroaroyl, acyloxy, aroyloxy, heteroaroyloxy, alkoxycarbonyl, nitro, cyano, halo, heteroaryl, heterocyclyl, aryl, ureido, arylurea, alkylurea, cycloalkylurea, alkylthiourea, aryloxy, aralkoxy, or —O(CH$_2$)$_n$COOH, —(CH$_2$)$_n$COOH, —C(O)O(CH$_2$)$_n$R, —(CH$_2$)$_n$N(H)C(O)OR, or —N(R')S(O)$_2$R wherein n is 1-4 and R is —H, alkyl, aryl or heteroaryl, multiple degrees of substitution being allowed. Examples of "aryl" groups include, but are not limited to, phenyl, 2-naphthyl, 1-naphthyl, biphenyl, as well as substituted derivatives thereof.

As used herein, the term "aralkyl" refers to an aryl or heteroaryl group, as defined herein, attached through a $C_1$-$C_3$ alkylene linker, wherein the $C_1$-$C_3$ alkylene is as defined herein. Examples of "aralkyl" include, but are not limited to, benzyl, phenylpropyl, 2-pyridylmethyl, 3-isoxazolylmethyl, 5-methyl-3-isoxazolylmethyl, and 2-imidazolyl ethyl.

As used herein, the term "heteroaryl" refers to a monocyclic five to seven membered aromatic ring, or to a fused bicyclic or tricyclic aromatic ring system comprising two of such monocyclic five to seven membered aromatic rings. These heteroaryl rings contain one or more nitrogen, sulfur, and/or oxygen heteroatoms, where N-oxides and sulfur oxides and dioxides are permissible heteroatom substitutions and may be optionally substituted with up to three members selected from a group consisting of $C_1$-$C_6$ alkyl, $C_1$-$C_6$ alkoxy, $C_1$-$C_6$ haloalkyl, $C_1$-$C_6$ haloalkoxy, $C_1$-$C_6$ alkylsulfanyl, $C_1$-$C_6$ alkylsulfenyl, $C_1$-$C_6$ alkylsulfonyl, $C_1$-$C_6$ alkylsulfonylamino, arylsulfonoamino, alkylcarboxy, alkylcarboxyamide, oxo, hydroxy, mercapto, amino optionally substituted by alkyl, aryl, or heteroaryl, carboxy, tetrazolyl, carboxamide, carbamoyl optionally substituted by alkyl, aryl, or heteroaryl, aminosulfonyl, acyl, aroyl, aroylamino, heteroaroyl, acyloxy, aroyloxy, heteroaroyloxy, alkoxycarbonyl, nitro, cyano, halo, heteroaryl, heterocyclyl, aryl, ureido, arylurea, alkylurea, cycloalkylurea, alkylthiourea, aryloxy, aralkoxy, or —O(CH$_2$)$_n$COOH, —(CH$_2$)$_n$COOH, —C(O)O(CH$_2$)$_n$R, —(CH$_2$)$_n$N(H)C(O)OR, or —N(R')S(O)$_2$R wherein n is 1-4 and R is —H, alkyl, aryl or heteroaryl, multiple degrees of substitution being allowed. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinazolinyl, quinolinyl, isoquinolinyl, benzofuranyl, benzothiophenyl, indolyl, indazolyl, and substituted versions thereof.

As used herein, the term "alkoxy" refers to the group $R_a$O—, where $R_a$ is alkyl as defined above and the terms "$C_1$-$C_3$ alkoxy" and "$C_1$-$C_6$ alkoxy" refer to an alkoxy group as defined herein wherein the alkyl moiety contains at least 1, and at most 3 or 6, carbon atoms. Exemplary "$C_1$-$C_3$ alkoxy" and "$C_1$-$C_6$ alkoxy" groups useful in the present invention include, but are not limited to, methoxy, ethoxy, n-propoxy, isopropoxy, n-butoxy, and t-butoxy.

As used herein, the term "amino" refers to the group —NH$_2$.

As used herein the term "alkylamino" refers to the group —NHR$_a$ wherein $R_a$ is alkyl as defined above.

As used herein the term "arylamino" refers to the group —NHR$_a$ wherein $R_a$ is aryl as defined above.

As used herein the term "aralkylamino" refers to the group —NHR$_a$ wherein $R_a$ is an aralkyl group as defined above.

As used herein the term "aralkoxy" refers to the group $R_bR_aO$—, where $R_a$ is alkylene and $R_b$ is aryl or heteroaryl all as defined above.

As used herein the term "aryloxy" refers to the group $R_aO$—, where $R_a$ is aryl or heteroaryl both as defined above.

As used herein the term "ureido" refers to the group —NHC(O)NH$_2$

As used herein, the term "arylurea" refers to the group —NHC(O)NHR$_a$R$_b$ wherein R$_a$ is aryl or heteroaryl and R$_b$ is —H, alkyl, or aryl as defined above.

As used herein, the term "arylthiourea" refers to the group —NHC(S)NHR$_a$ wherein R$_a$ is aryl as defined above.

As used herein, the term "alkylurea" refers to the group —NHC(O)NR$_a$R$_b$ wherein R$_a$ is alkyl and R$_b$ is —H or alkyl as defined above.

As used herein, the term "cycloalkylurea" refers to the group —NHC(O)NHR$_a$ wherein R$_a$ is cycloalkyl as defined above.

As used herein, the term "$C_3$-$C_7$ cycloalkoxy" refers to the group R$_a$O—, where R$_a$ is $C_3$-$C_7$ cycloalkyl as defined above. Exemplary $C_3$-$C_7$ cycloalkoxy groups useful in the present invention include, but are not limited to, cyclobutoxy, and cyclopentoxy.

As used herein, the term "haloalkoxy" refers to the group R$_a$O—, where R$_a$ is haloalkyl as defined above and the term "$C_1$-$C_6$ haloalkoxy" refers to a haloalkoxy group as defined herein wherein the haloalkyl moiety contains at least 1, and at most 6, carbon atoms. Exemplary $C_1$-$C_6$ haloalkoxy groups useful in the present invention include, but is not limited to, trifluoromethoxy.

As used herein, the term "alkylsulfanyl" refers to the group R$_a$S—, where R$_a$ is alkyl as defined above and the term "$C_1$-$C_6$ alkylsulfanyl" refers to an alkylsulfanyl group as defined herein wherein the alkyl moiety contains at least 1, and at most 6, carbon atoms.

As used herein, the term "haloalkylsulfanyl" refers to the group R$_a$S—, where R$_a$ is haloalkyl as defined above and the term "$C_1$-$C_6$ haloalkylsulfanyl" refers to a haloalkylsulfanyl group as defined herein wherein the alkyl moiety contains at least 1, and at most 6, carbon atoms.

As used herein, the term "alkylsulfenyl" refers to the group R$_a$S(O)—, where R$_a$ is alkyl as defined above and the term "$C_1$-$C_6$ alkylsulfenyl" refers to an alkylsulfenyl group as defined herein wherein the alkyl moiety contains at least 1, and at most 6, carbon atoms.

As used herein, the term "alkylsulfonyl" refers to the group R$_a$S(O)$_2$—, where R$_a$ is alkyl as defined above and the term "$C_1$-$C_6$ alkylsulfonyl" refers to an alkylsulfonyl group as defined herein wherein the alkyl moiety contains at least 1, and at most 6, carbon atoms.

As used herein, the term "alkylsulfonylamino" refers to the group —NR$_b$S(O)$_2$R$_a$ wherein R$_a$ is alkyl and R$_b$ is —H or $C_1$-$C_6$ alkyl as defined above, and the term "$C_1$-$C_6$ alkylsulfonylamino" refers to an alkylsulfonylamino group as defined herein wherein the alkyl moiety contains at least 1, and at most 6, carbon atoms.

As used herein, the term "arylsulfonylamino" refers to the group —NR$_b$S(O)$_2$R, wherein R$_a$ is aryl or heteroaryl and R$_b$ is —H or $C_1$-$C_6$ alkyl as defined above.

As used herein, the term "alkylcarboxyamide" refers to the group —NHC(O)R$_a$ wherein R$_a$ is alkyl, amino, or amino substituted with alkyl, aryl or heteroaryl as described above.

As used herein the term "alkylcarboxy" refers to the group —C(O)R$_a$ wherein R$_a$ is alkyl as described above.

As used herein, the term "oxo" refers to the group =O.

As used herein, the term "mercapto" refers to the group —SH.

As used herein, the term "carboxy" refers to the group —C(O)OR$_a$, wherein R$_a$ is H or alkyl as defined herein.

As used herein, the term "cyano" refers to the group —CN.

As used herein the term "cyanoalkyl" refers to the group —R$_a$CN wherein R$_a$ is alkyl as defined above. Exemplary "cyanoalkyl" groups useful in the present invention include, but are not limited to, cyanomethyl, cyanoethyl, and cyanoisopropyl.

As used herein, the term "aminosulfonyl" refers to the group —S(O)$_2$R$_a$R$_b$ wherein R$_a$ and R$_b$ are independently H, $C_1$-$C_6$ alkyl, aryl, aralkyl, or heteroaryl.

As used herein, the term "carbamoyl" refers to the group —OC(O)NHR$_a$, where R$_a$ is hydrogen or alkyl as defined herein.

As used herein, the term "carboxamide" refers to the group —C(O)NR$_a$R$_b$ wherein R$_a$ and R$_b$ are independently H, $C_1$-$C_6$ alkyl, aryl, aralkyl, or heteroaryl.

As used herein, the term "sulfanyl" shall refer to the group —S—.

As used herein, the term "sulfenyl" shall refer to the group —S(O)—.

As used herein, the term "sulfonyl" shall refer to the group —S(O)$_2$— or —SO$_2$—.

As used herein, the term "acyl" refers to the group R$_a$C(O)—, where R$_a$ is alkyl, cycloalkyl, or heterocyclyl as defined herein.

As used herein, the term "aroyl" refers to the group R$_a$C(O)—, where R$_a$ is aryl as defined herein.

As used herein, the term "aroylamino" refers to the group R$_a$C(O)NH—, where R$_a$ is aryl as defined herein.

As used herein, the term "heteroaroyl" refers to the group R$_a$C(O)—, where R$_a$ is heteroaryl as defined herein.

As used herein, the term "alkoxycarbonyl" refers to the group R$_a$OC(O)—, where R$_a$ is alkyl as defined herein.

As used herein, the term "acyloxy" refers to the group R$_a$C(O)O—, where R$_a$ is alkyl, cycloalkyl, or heterocyclyl as defined herein.

As used herein, the term "aroyloxy" refers to the group R$_a$C(O)O—, where R$_a$ is aryl as defined herein.

As used herein, the term "heteroaroyloxy" refers to the group R$_a$C(O)O—, where R$_a$ is heteroaryl as defined herein.

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5$^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers. The compounds of this invention include mixtures of enantiomers as well as purified enantiomers or enantiomerically enriched mixtures. Also included within the scope of the invention are the individual isomers of the compounds represented by formula (I) above as well as any wholly or partially equilibrated mixtures thereof. The present invention also covers the individual isomers of the compounds represented by the formulas above as mixtures with isomers thereof in which one or more chiral centers are inverted. Also, it is understood that any tautomers and mixtures of tautomers of the compounds of formula (I) are included within the scope of the compounds of formula (I).

It is to be understood that reference to compounds of formula (I) above, following herein, refers to compounds within the scope of formula (I) as defined above with respect to A, D, q, m, n, R, R', $R^1$, $R^2$, $R^3$, $R^4$, $R^5$, and $R^6$ unless specifically limited otherwise.

As recited above, various substituents, such as A, may be aryl or heteroaryl. It is understood that such aryl or heteroaryl groups may be substituted as indicated above in the definitions for "aryl" and "heteroaryl". Alternatively, the aryl or heteroaryl groups may be substituted by at least one $R^1$, wherein $R^1$ is as defined above.

In one embodiment, A is aryl or heteroaryl each optionally substituted with at least one group $R^1$. In one embodiment, A is aryl optionally substituted with at least one group $R^1$, preferably, A is phenyl or phenyl substituted by at least one $R^1$, more preferably A is phenyl substituted by at least one $R^1$. In another embodiment, A is heteroaryl optionally substituted with at least one group $R^1$. Wherein $R^1$ is as defined above.

In one embodiment, A is $C_1$-$C_6$ alkenyl or $C_1$-$C_6$ alkynyl. In another embodiment, A is —CN, —COOH, or —C(O)NR$^4$R$^5$. In a further embodiment, A is —NRR', —N(R')S(O)$_2$R, —N(R')C(O)R, or —N(R')C(O)NR$^4$R$^5$. Wherein R, R', R$^4$ and R$^5$ are as defined above.

In one embodiment, D is

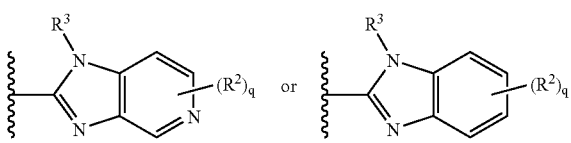

wherein q, $R^2$ and $R^3$ are as defined above.

In another embodiment, D is

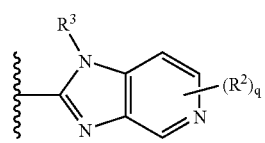

wherein q, $R^2$ and $R^3$ are as defined above.

In still another embodiment, D is

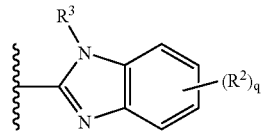

wherein q, $R^2$ and $R^3$ are as defined above.

In an alternative embodiment, D is

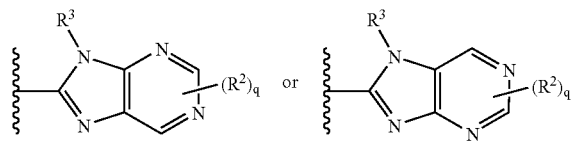

wherein q, $R^2$ and $R^3$ are as defined above.

In another embodiment, D is

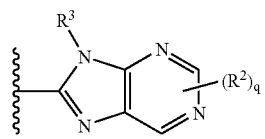

wherein q, $R^2$ and $R^3$ are as defined above.

In still another embodiment, D is

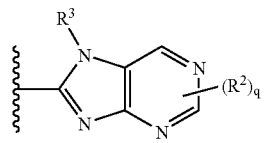

wherein q, $R^2$ and $R^3$ are as defined above.

Specific examples of compounds of the present invention include the following:

3-(1-ethyl-1H-imidazo[4,5-c]pyridin-2-yl)pyrazin-2-amine;
5-bromo-3-(1-ethyl-1H-imidazo[4,5-c]pyridin-2-yl)pyrazin-2-amine;
3-(1-ethyl-1H-imidazo[4,5-c]pyridin-2-yl)-5-phenylpyrazin-2-amine;
3-(1-ethyl-1H-imidazo[4,5-c]pyridin-2-yl)-5-(3,4,5-trimethoxyphenyl)pyrazin-2-amine;
3-(1-ethyl-1H-imidazo[4,5-c]pyridin-2-yl)-5-(4-fluorophenyl)pyrazin-2-amine;
3-(1-ethyl-1H-imidazo[4,5-c]pyridin-2-yl)-5-thien-2-ylpyrazin-2-amine;
5-(4-aminophenyl)-3-(1-ethyl-1H-imidazo[4,5-c]pyridin-2-yl)pyrazin-2-amine;
3-(1-ethyl-1H-imidazo[4,5-c]pyridin-2-yl)-5-pyridin-3-ylpyrazin-2-amine;
3-(1-ethyl-1H-imidazo[4,5-c]pyridin-2-yl)-5-(1H-indol-5-yl)pyrazin-2-amine;
3-[1-(2-methoxyethyl)-1H-benzimidazol-2-yl]-5-thien-2-ylpyrazin-2-amine;
3-(1H-benzimidazol-2-yl)-5-(3-fluorophenyl)pyrazin-2-amine;

3-(1H-benzimidazol-2-yl)-5-(4-fluorophenyl)pyrazin-2-amine;
4-[5-amino-6-(1-ethyl-1-H-imidazo[4,5-c]pyridin-2-yl)pyrazin-2-yl]-N,N-dimethylbenzenesulfonamide;
3-(1-ethyl-1-H-imidazo[4,5-c]pyridin-2-yl)-5-[3-(methylsulfonyl)phenyl]pyrazin-2-amine;
3-{4-[5-amino-6-(1-ethyl-1-H-imidazo[4,5-c]pyridin-2-yl)pyrazin-2-yl]phenyl}propanoic acid;
{4-[5-amino-6-(1-ethyl-1-H-imidazo[4,5-c]pyridin-2-yl)pyrazin-2-yl]phenoxy}acetic acid;
{3-[5-amino-6-(1-ethyl-1-H-imidazo[4,5-c]pyridin-2-yl)pyrazin-2-yl]phenoxy}acetic acid;
N-{4-[5-amino-6-(1-ethyl-1-H-imidazo[4,5-c]pyridin-2-yl)pyrazin-2-yl]phenyl}methanesulfonamide;
benzyl 4-[5-amino-6-(1-ethyl-1-H-imidazo[4,5-]pyridin-2-yl)pyrazin-2-yl]benzoate;
5-[4-(benzyloxy)phenyl]-3-(1-ethyl-1-H-imidazo[4,5-c]pyridin-2-yl)pyrazin-2-amine;
5-[1,1'-biphenyl-3-yl)-3-(1-ethyl-1-H-imidazo[4,5-c]pyridin-2-yl)pyrazin-2-amine;
4-[5-amino-6-(1-ethyl-1-H-imidazo[4,5-c]pyridin-2-yl)pyrazin-2-ylbenzoic acid;
tert-butyl 3-[5-amino-6-(1-ethyl-1-H-imidazo[4,5c]pyridin-2-yl)pyrazin-2-yl]benzylcabamate;
3 (1-ethyl-1H-imidazo[4,5-c]pyridin-2-yl)-5-(1H-pyrrol-2-yl)pyrazin-2-amine;
3 (1-ethyl-1H-imidazo[4,5-c]pyridin-2-yl)-5-(1H-indol-2-yl)pyrazin-2-amine; and
5-[(4-aminophenyl)ethynyl]-3-(1-ethyl-1H-imidazo[4,5-c]pyridin-2-yl)pyrazin-2-amine;

or a salt, solvate, or physiologically functional derivative thereof.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula (I), as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula (I) and salts, solvates and physiological functional derivatives thereof, and one or more pharmaceutically acceptable carriers, diluents or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I), and salts, solvates and physiological functional derivatives thereof, can also be administered in the form of liposome delivery systems, such as small unilamellar vesicles, large unilamellar vesicles and multiamellar vesicles. Liposomes can be formed from a variety of phospholipids, such as cholesterol, stearylamine or phosphatidylcholines.

The compounds of formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the human or other animal, the precise condition requiring treatment and its severity, the nature of the formulation, and the route of administration, and will ultimately be at the discretion of the attendant physician or veterinarian. However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to above.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Working Examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I).

Compounds of general formula (I) can be prepared according to the synthetic sequences illustrated in Schemes 1-6 and further detailed in the Examples section following.

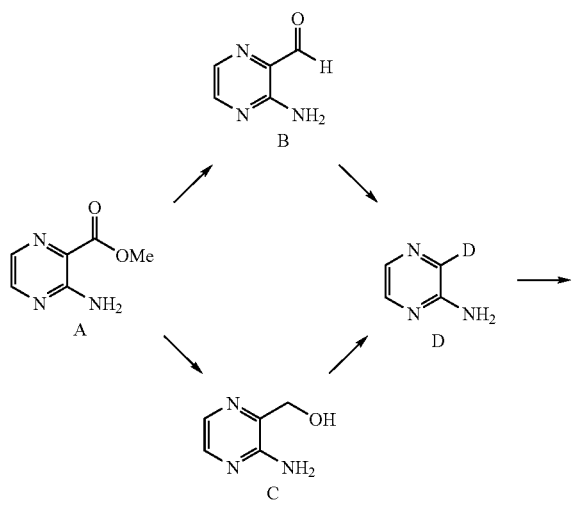

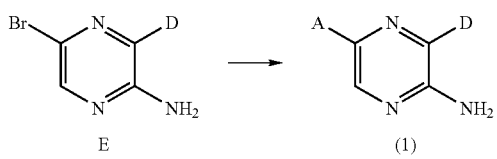

As illustrated in Scheme 1, compounds of general formula (I) may be synthesized starting with compound A, ethyl-3-aminopyrazine-2-carboxylate. A can be converted by reduction using an appropriate reagent, such as DIBALH or LAH, to either aldehyde B or alcohol C. One way these intermediates A and B can be converted to intermediate D is by condensation with a substituted phenylenediamine or heterocyclic ortho dianiline (for example intermediates O and R in scheme 5 below) in an appropriate solvent at temperatures between 30 and 250° C., often in the presence of an appropriate additive. For example, heating aldehyde B or alcohol C, appropriate substituted or heterocyclic phenylenediamine O or R and $NaHSO_3$ in dimethylacetamide at 200° C. in a microwave for 10 minutes provides compounds of formula D.

Compounds of formula E may be synthesized by reaction of compounds D with a suitable brominating agent in a suitable solvent. There are a variety of conditions known in the chemical literature that are useful for halogenating an aromatic ring. For example, one can utilize N-bromosuccinimide in THF.

Compounds of general formula (I) can be synthesized from compounds of general formula E through a variety of metal mediated coupling reactions well known to those skilled in the art. For example, reaction of aryl halides such as E with an aryl tin species or an aryl boronic acid species can be carried out in an appropriate solvent in the presence of an appropriate catalyst and an appropriate base at a temperature between 30° C. and 250° C. These reactions (Suzuki reaction with an aryl boronic acid and Stille reaction with an aryl tin reagent) are well described in the literature, and a number of catalyst, base, solvent, and temperature combinations have proven useful. For example, heating an appropriate compound of general formula E with an aryl boronic acid, aqueous sodium carbonate and dichlorobis(triphenylphosphine)palladium(II) in dimethoxyethane at 150° C. for 10 minutes in a SmithSynthesizer microwave is one method useful for synthesis of products of general formula (I). Other well described reactions such as the Heck reaction, Sonogashira reaction, carbonylation reactions and cyanation reactions may be used to generate other compounds of general formula (I) that replace the bromine of compounds E with different functionality, such as substituted olefins, substituted acetylenes, substituted amides, a carboxylic acid, or nitrile. Like the Suzuki and Stille reactions, a number of catalyst, base, solvent, and temperature combinations have proven useful to carry out the Sonogashira reactions, Heck reactions, carbonylation reactions, and cyanations.

Scheme 2

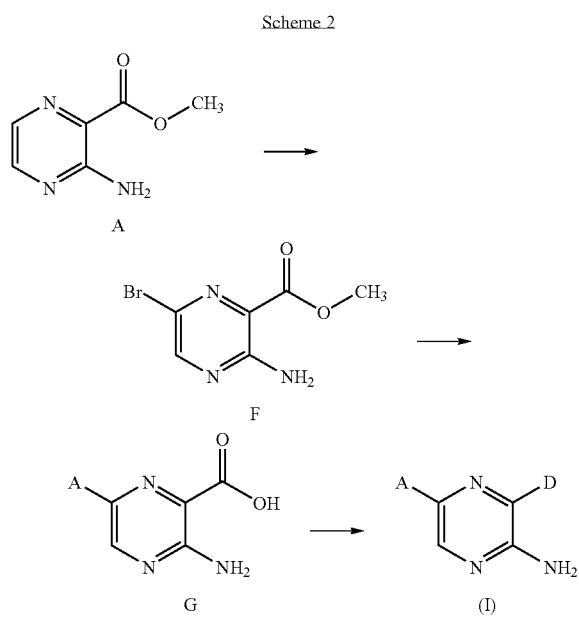

Compounds of general formula (I) may also be synthesized as depicted in scheme 2. Compound of formula F may be synthesized by reaction of compound A, ethyl-3-aminopyrazine-2-carboxylate, with a suitable brominating agent in a suitable solvent. There are a variety of conditions known in the chemical literature that are useful for halogenating an aromatic ring. For example, one can utilize N-bromosuccinimide in THF. Compounds of general formula G can be synthesized by a variety of metal mediated coupling reactions that are well-described in the literature and known to one skilled in the art. These include, but are not limited to, Heck reactions, Suzuki reactions, Stille reactions, Sonogashira reactions, carbonylation reactions, and cyanation reactions. For all of these types of reactions, a number of catalyst, base, solvent, and temperature combinations have been explored and have proven useful for carrying out the desired transformation. Compounds of general formula (I) may be synthesized from compounds of general formula G by reaction with a substituted phenylenediamine or heterocyclic ortho dianiline (for example intermediates O and R in scheme 5 below) in an appropriate solvent at temperatures between 30 and 250° C., often in the presence of an appropriate additive. For example, reaction of a compound of general formula G, an appropriate substituted or heterocyclic phenylenediamine O or R, diethyl cyanophosphonate, and triethylamine in dimethoxyethane as solvent at 200° C. for 10 min in the SmithSynthesizer microwave affords compounds of general formula (I).

Scheme 3

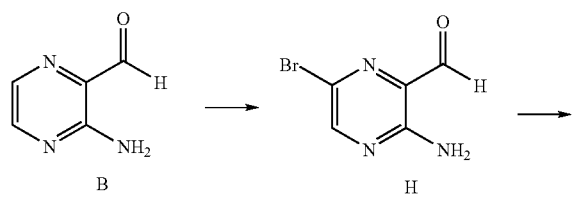

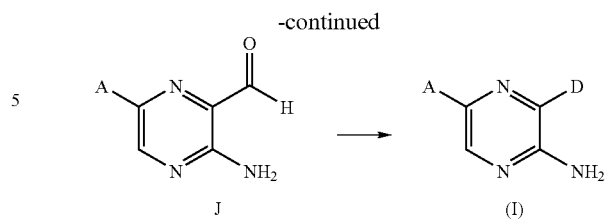

Scheme 3 depicts an alternate way to synthesize compounds of general formula (I). Compound H can be synthesized by reaction of compound B with a suitable brominating agent in a suitable solvent at a suitable temperature. There are a variety of conditions known in the chemical literature that are useful for halogenating an aromatic ring. For example, one can utilize N-bromosuccinimide in THF. Compound H can then be subjected to a variety of coupling reactions that are well-described in the literature and known to one skilled in the art. These include, but are not limited to, Heck reactions, Suzuki reactions, Stille reactions, Sonogashira reactions, carbonylation reactions, and cyanation reactions. For all of these types of reactions, a number of catalyst, base, solvent, and temperature combinations have been explored and have proven useful for carrying out the desired transformation. Application of these sorts of conditions, as described above and further illustrated in the detailed examples following, give compounds of general formula J. Compound of general formula J can be converted into compounds of general formula (I) by condensation with a substituted phenylenediamine or heterocyclic ortho dianiline (for example intermediates O and R in scheme 5 below) in an appropriate solvent at temperatures between 30 and 250° C., often in the presence of an appropriate additive.

Intermediates used in schemes 1, 2, and 3 can be obtained from commercial sources or synthesized by one skilled in the art. Some of the intermediates may be synthesized, for example, by the synthetic sequences outlined in schemes 4, 5, and 6, and further detailed in the experimental sections following.

Scheme 4

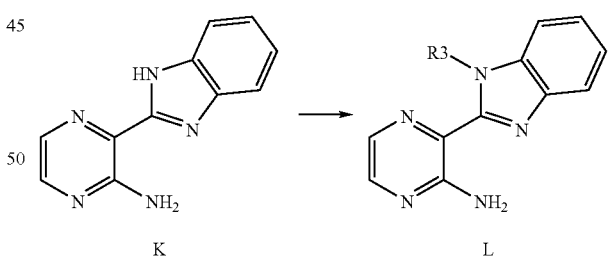

Scheme 4 illustrates the alkylation of a benzimidazole with an appropriate R3 group. This transformation can be carried out by reaction of a compound such as K, in an appropriate solvent, with a suitable base and an appropriate alkylating agent, at a suitable temperature. For example, reaction of K with 2-bromoethyl methyl ether and cesium carbonate in DMF as solvent at ambient temperature gives a compound L with R3 being a methoxy ethyl moiety. There are a wide variety of alkylating agents commercially available, and they are also readily synthesized by one skilled in the art. Scheme 4 illustrates alkylation of the benzmidazole ring in particular. As noted previously, the "D" group of general formula (I)

may include not only substituted benzimidazoles, but other heterocyclic systems as well. One skilled in the art will recognize that these other systems may be alkylated to incorporate an R3 group in a similar manner as to that depicted in scheme 4 for the benzimidazole case.

Scheme 5

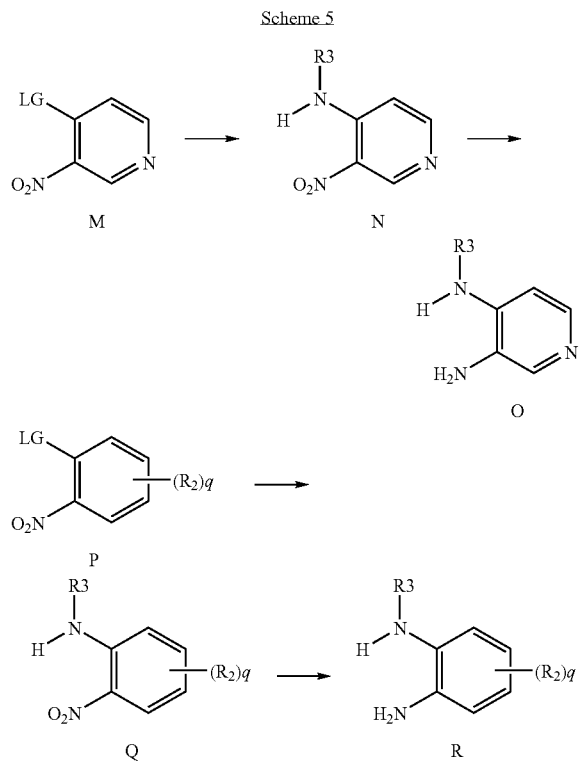

Substituted ortho-phenylene diamines and heterocyclic ortho-di-anilines are used in the transformations described in schemes 1, 2, and 3. Some of these are commercially available. Others may be synthesized by known methods, including the method depicted in scheme 5. In this scheme, molecules of general structure O and R are prepared by reduction of the nitro group of compounds of general formula N and Q. Nitro groups may be reduced by a variety of methods, including hydrogenation in an appropriate solvent in the presence of an appropriate catalyst such as Palladium on Carbon, or with tin (II) chloride in an appropriate solvent. Other methods for nitro reduction can be found in the book *Comprehensive Organic Transformations* by Richard LaRock. Compounds of general formula N and Q can be synthesized by reaction of an appropriate substituted amine (R3-NH2) with compounds such as M and P. "LG" in the general structures M and P stands for "leaving group" and represents, for example, fluoro, chloro, bromo, or methoxy, or other groups that can be displaced by a nucleophile at an appropriate temperature in an appropriate solvent.

Scheme 6

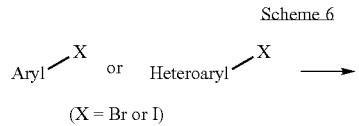

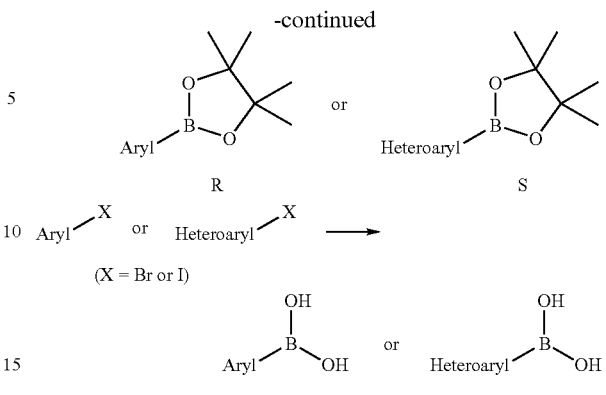

In some instances, the chemistry depicted in schemes 1, 2, and 3 that describe the synthesis of compounds of general formula (I) make use of boronic acids or boronate esters. Many boronic acids and boronate esters are commercially available. When not commercially available, boronic acids and boronate esters may be synthesized by standard methods, including those depicted in scheme 6. Heteroaryl or aryl boronate esters may be synthesized by reaction of an aryl or heteroaryl halide with bis(pinacolato)diboron and an appropriate palladium catalyst in an appropriate solvent with appropriate additives. For example, reaction of an aryl halide and bis(pinacolato)diboron with $PdCl_2(dppf)_2$, and potassium acetate, in DMF as solvent at 80° C. for 90 minutes can give boronate esters of general formula R. Heteroaryl or aryl boronic acids may be synthesized by treating an appropriate aryl halide or heteroaryl halide with a strong base such as n-BuLi or t-BuLi in a solvent such as THF or dioxane, followed by reaction of the intermediate organometallic species with a reagent to introduce the boron. For example, reaction of an aryl halide in THF at −70° C. with n-butyl lithium, followed by addition of tri-isopropylborate gives, after standard work up, aryl boronic acids of general formula T.

Certain embodiments of the present invention will now be illustrated by way of example only. The physical data given for the compounds exemplified is consistent with the assigned structure of those compounds.

EXAMPLES

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams); mg (milligrams);
L (liters); mL (milliliters);
μL (microliters); psi (pounds per square inch);
M (molar); mM (millimolar);
i.v. (intravenous); Hz (Hertz);
MHz (megaHertz); mol (moles);
mmol (millimoles); rt (room temperature);
min (minutes); h (hours);

mp (melting point); TLC (thin layer chromatography);
T$_r$ (retention time); RP (reverse phase);
MeOH (methanol); i-PrOH (isopropanol);
TEA (triethylamine); TFA (trifluoroacetic acid);
TFM (trifluoroacetic anhydride); THF (tetrahydrofuran);
DMSO (dimethylsulfoxide); AcOEt (ethyl acetate);
DME (1,2-dimethoxyethane); DCM (dichloromethane);
DCE (dichloroethane); DMF (N,N-dimethylformamide);
DMPU (N,N'-dimethylpropyleneurea); CDI (1,1'-carbonyl-diimidazole); IBCF
(isobutyl chloroformate); HOAc (acetic acid);
HOSu (N-hydroxysuccinimide); HOBT (1-hydroxybenzotriazole);
mCPBA (meta-chloroperbenzoic acid);
EDC (1-[(3-dimethylamino)propyl]-3-ethylcarbodiimide hydrochloride);
BOC (tert-butyloxycarbonyl); FMOC (9-fluorenylmethoxycarbonyl); DCC (dicyclohexylcarbodiimide); CBZ (benzyloxycarbonyl);
Ac (acetyl); atm (atmosphere);
TMSE (2-(trimethylsilyl)ethyl); TMS (trimethylsilyl);
TIPS (triisopropylsilyl); TBS (t-butyldimethylsilyl);
DMAP (4-dimethylaminopyridine); BSA (bovine serum albumin)
ATP (adenosine triphosphate); HRP (horseradish peroxidase);
DMEM (Dulbecco's modified Eagle medium);
HPLC (high pressure liquid chromatography);
BOP (bis(2-oxo-3-oxazolidinyl)phosphinic chloride);
TBAF (tetra-n-butylammonium fluoride);
HBTU(O-Benzotriazole-1-yl-N,N,N',N'-tetramethyluroniumhexafluoro phosphate).
HEPES (4-(2-hydroxyethyl)-1-piperazine ethane sulfonic acid);
DPPA (diphenylphosphoryl azide);
fHNO$_3$ (fuming HNO$_3$); and
EDTA (ethylenediaminetetraacetic acid).

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.

$^1$H NMR spectra were recorded on a Varian VXR-300, a Varian Unity-300, a Varian Unity-400 instrument, a Brucker AVANCE-400, or a General Electric QE-300. Chemical shifts are expressed in parts per million (ppm, δ units). Coupling constants are in units of Hertz (Hz). Splitting patterns describe apparent multiplicities and are designated as s (singlet), d (doublet), t (triplet), q (quartet), quint (quintet), m (multiplet), br (broad).

HPLC were recorded on a Gilson HPLC or Shimadzu HPLC system by the following conditions. Column: 50×4.6 mm (id) stainless steel packed with 5 □m Phenomenex Luna C-18; Flow rate: 2.0 mL/min; Mobile phase: A phase=50 mM ammonium acetate (pH 7.4), B phase=acetonitrile, 0-0.5 min (A: 100%, B: 0%), 0.5-3.0 min (A:100-0%, B:0-100%), 3.0-3.5 min (A: 0%, B: 100%), 3.5-3.7 min (A: 0-100%, B: 100-0%), 3.7-4.5 min LA: 100%, B: 0%); Detection: UV 254 nm; Injection volume: 3 □L.

Low-resolution mass spectra (MS) were recorded on a JOEL JMS-AX505HA, JOEL SX-102, or a SCIEX-APIiii spectrometer; LC-MS were recorded on a micromass 2MD and Waters 2690; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. Most of the reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230-400 mesh, Merck).

Example 1

3-(1-ethyl-1H-imidazo[4,5-c]pyridin-2-yl)pyrazin-2-amine

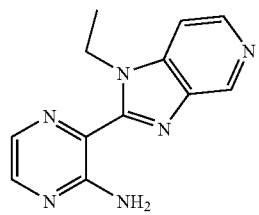

(a) Preparation of Ethyl-(3-nitropyridin-4-yl)amine

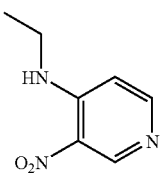

4Methoxy-3-nitropyridine hydrochloride (11.2 g, 58.9 mmol) in ethanol (75 ml) was treated with a 70% solution of ethylamine in water (64 ml) and heated under reflux for 2 hours. After cooling to room temperature, the solvent was removed in vacuo and the residue dissolved in ethyl acetate and water. The mixture was extracted (×3) with ethyl acetate, washed with water and saturated aqueous sodium chloride solution before drying over magnesium sulfate. Evaporation of the solvent afforded the title compound (11.7 g, 96%).

NMR 1H NMR (400 MHz, DMSO-D6) δ ppm 1.18 (t, J=7.14 Hz, 3H), 3.41 (m, 2H), 6.98 (d, J=6.32 Hz, 1H), 8.24 (d, J=6.32 Hz, 1H), 8.39 (br, 1H), 9.00 (s, 1H), MS m/z 168 (M+1)$^+$.

(b) Preparation of N$^4$-ethylpyridine-3,4-diamine

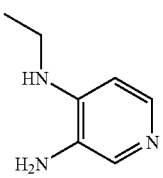

Ethyl-(3-nitropyridin-4-yl)amine (8.7 g, 52.0 mmol) in ethanol (150 ml) was hydrogenated for 18 hours in the presence of 10% palladium on carbon. After filtration of the catalyst through celite, the filtrate was concentrated in vacuo to afford the title compound (6.7 g, 94%).

1H NMR (400 MHz, DMSO-D6) δ ppm 1.19 (m, 3H), 3.09 (m, 2H), 4.53 (br, 2H), 5.21 (br, 1H), 6.31 (d, J=5.22 Hz, 1H), 7.57 (d, J=5.36 Hz, 1H), 7.62 (s, 1H). MS (ES+) m/e 138 [M+H]+

(c) Preparation of: 3-aminopyrazine-2-carbaldehyde

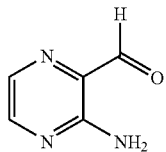

Methyl-3-aminopyrazine-2-carboxylate (11 g) was dissolved in THF and cooled to −78° C. Diisobutylaluminum hydride (1M in hexanes, 250 mL) was added, and the reaction stirred at −78° C. for 4 hours. The reaction was then warmed to 0° C. for one hour before being quenched slowly by addition of 1M hydrochloric acid. Ethyl acetate was added and the layers separated. The organic layer was dried over magnesium sulfate, filtered and concentrated. The residue was triturated in hexanes to afford title compound (3.0 g, 34%).

1H NMR (400 MHz, DMSO-D6) δ ppm 7.73 (br, 2H), 8.07 (d, J=2.25 Hz, 1H), 8.36 (d, J=2.11 Hz, 1H), 9.95 (s, 1H)

(d) Preparation of: 3-(1-ethyl-1H-imidazo[4,5-c]pyridin-2-yl)pyrazin-2-amine

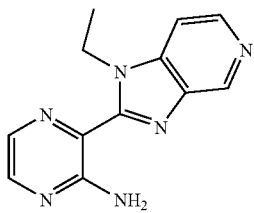

3-aminopyrazine-2-carbaldehyde (made in example 1(c)) (0.30 g, 2.4 mmol), N4-ethylpyridine-3,4-diamine (made in example 1(b)) (0.36 g, 2.6 mmol), and sodium hydrogensulfite (0.30 g) were combined in 3 mL of dimethylacetamide and heated to 200° C. in a SmithSynthesizer microwave for 10 minutes. The reaction mixture was partitioned between ethyl acetate and water. The reaction was extracted with ethyl acetate (×3), and the combined organic layers were washed with water and saturated aqueous sodium chloride solution, and dried over magnesium sulfate. After filtration, the organics were concentrated in vacuo. Trituration with diethyl ether affords the title compound as tan solids (0.46 g, 80%).

1H NMR (400 MHz, DMSO-D6) δ ppm 1.37 (t, J=7.14 Hz, 3H), 4.82 (q, J=6.87 Hz, 2H), 7.76 (d, J=6.18 Hz, 1H), 8.01 (d, J=2.06 Hz, 1H) 8.07 (br, 2H), 8.17 (d, J=2.34 Hz, 1H), 8.42 (d, J=5.50, 1H) 9.05 (s, 1H) MS m/z 241 (M+1)+.

Alternate Preparation of Example 1

(a) Preparation of (3-amino-pyrazin-2-yl)-methanol

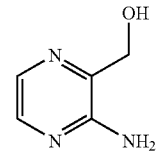

Methyl-3-aminopyrazine-2-carboxylate (14.22 g, 93 mmol) was suspended in tetrahydrofuran (1 L) and cooled under a nitrogen atmosphere in a methanol/ice bath. Lithium aluminium hydride (100 ml, 1 M solution in diethyl ether, 100 mmol) was added at such a rate to maintain the temperature between 8-10° C. Once addition was complete the reaction was stirred at room temperature for 3 hours and then heated at reflux for 20 minutes. The reaction was then cooled to 0° C. and quenched with water (30 mL in 100 mL tetrahydrofuran) keeping the temperature below 8° C. The reaction was then stirred at room temperature for 30 minutes and then filtered. The residue was washed with hot ethyl acetate (250 mL×2) filtered. The two filtrates were combined and evaporated to dryness. This produced (3-amino-pyrazin-2-yl)methanol (7.38 g) as a pale orange solid.

1H NMR (400 MHz, DMSO-D6) δ ppm 4.47 (d, J=5.27 Hz, 2H) 5.29 (t, J=5.52 Hz, 1 H) 6.18 (brs, 2H) 7.66 (d, J=2.76 Hz, 1H) 7.85 (d, J=0.76 Hz, 1H).

(b) Preparation of 3-(1-ethyl-1H-imidazo[4,5-c]pyridin-2-2yl)pyrazin-2-amine

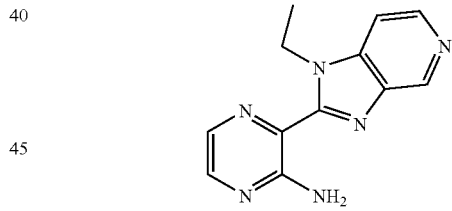

(3-amino-pyrazin-2-yl)-methanol (180 mg, 1.44 mmol), N-4-ethyl-pyridine-3,4-diamine (296 mg, 2.16 mmol), sodium hydrogensulfite (360 mg, 3.45 mmol) and N,N dimethyacetamide (4 mL) were combined, stirred for 20 seconds, and heated in the microwave (200° C. for 600 seconds). The residue was taken up in water (20 mL) and extracted with ethyl acetate (3×20 mL). The ethyl acetate layers were combined, dried over magnesium sulfate, filtered and the solvent removed in vacuo. The residue was dissolved in methanol (50 mL) and preabsorbed onto silica (1 g). The product was purified using the ISCO combiflash SQ16X eluting with a mix of dichloromethane, ethanol and ammonia (100% dichloromethane to 20% ethanol 79% dichloromethane 1% ammonia). The desired fractions were combined and solvent removed in vacuo to yield 3-(1-ethyl-1H-imidazo[4,5-c]pyridin-2-2yl)pyrazin-2-amine (171 mg) as a pale yellow solid.

1H NMR (400 MHz, DMSO-D6) δ ppm 1.38 (t, J=7.03 Hz, 3H) 4.83 (q, J=7.02 Hz, 2H) 7.77 (d, J=5.53 Hz, 1H) 8.02 (d, J=2.26 Hz, 1H) 8.19 (d, J=2.26 Hz, 1H) 8.44 (d, J=5.53 Hz, 1H) 9.07 (s, 1H) MS m/z 241 (M+1)+.

Example 2

5-bromo-3-(1-ethyl-1H-imidazo[4,5-c]pyridin-2-yl)pyrazin-2-amine

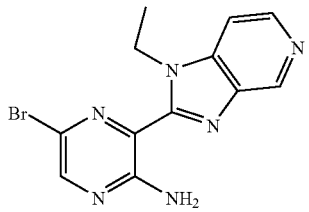

To a solution of 3-(1-ethyl-1H-imidazo[4,5-c]pyridin-2-yl)pyrazin-2-amine (0.45 g, 1.8 mmol) (see Example 1) in THF is added N-bromosuccinimide (0.37 g, 2.1 mmol). The reaction is stirred for 4 hours at ambient temperature. Sodium sulfite (excess) was added and stirred vigorously for 30 minutes. The mixture was then concentrated to dryness and treated with water. After sonication, the solids were collected on filter. Rinsing (×2) with diethyl ether afforded 5-bromo-3-(1-ethyl-1H-imidazo[4,5-c]pyridin-2-yl)pyrazin-2-amine (0.47 g, 79%) as tan solids.

1H NMR (400 MHz, DMSO-D6) δ ppm 1.45 (t, J=7.16 Hz, 3H) 4.79 (q, J=7.02 Hz, 2H) 7.82 (dd, J=5.62 0.84 Hz, 1H), 8.38 (s, 1H), 8.49 (d, J=5.76 Hz, 1H) 9.12 (d, J=0.56 Hz, 1H) MS m/z 318/320 (M+1)+

Example 3

3-(1-ethyl-1H-imidazo[4,5-c]pyridin-2-yl)-5-phenylpyrazin-2-amine

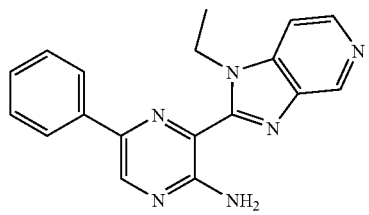

5-Bromo-3-(1-ethyl-1H-imidazo[4,5-c]pyridin-2-yl)pyrazin-2-amine (0.038 g, 0.12 mmol) (see Example 2), phenyl boronic acid (0.034 g, 0.27 mmol), dichlorobis(triphenylphosphine)palladium(II) (0.009 g, 0.012 mmol), potassium carbonate (0.045 g, 0.32 mmol), and an 8:1 mixture of acetonitrile:water (3 mL) were combined and subjected to 150° C. for 5 minutes in a SmithSynthesizer microwave. The resulting heterogeneous, black mixture was filtered through a celite pad, which was then washed with ethyl acetate and water. The mixture is extracted into ethyl acetate (×3) and washed with water and saturated sodium chloride. The combined organic layers are dried over magnesium sulfate, filtered and concentrated. The residue is purified on silica, eluting with 2.5% methanol in chloroform to afford the title compound (0.009 g, 23%).

1H NMR (400 MHz, DMSO-D6) δ ppm 1.51 (t, J=6.77 Hz, 3H), 4.99 (q, J=6.96 Hz, 2H), 7.42 (m, 1H), 7.54 (m, 2H), 7.83 (dd, J=5.68 Hz, 1.10 Hz, 1H), 8.02 (m, 2H), 8.47 (d, J=5.68 Hz, 1H), 8.84 (s, 1H), 9.11 (d, J=0.92 Hz, 1H) MS m/z 317 (M+1)+.

Example 4

3-(1-ethyl-1H-imidazo[4,5-c]pyridin-2-yl)-5-(3,4,5-trimethoxyphenyl)pyrazin-2-amine

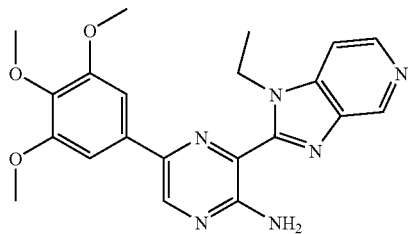

The title compound was synthesized using the general Suzuki reaction procedure recited in Example 3, except 2,3,4-trimethoxyphenylboronic acid was utilized.

1H NMR (400 MHz, DMSO-D6) δ ppm 1.51 (t, J=7.42 Hz, 3H), 3.71(s, 3H), 3.89 (s, 6H), 4.99 (q, J=7.28 Hz, 2H), 7.28 (s, 2H), 7.79 (t, J=6.05 Hz, 1H), 8.45 (t, J=6.05 Hz, 1H), 8.87 (s, 1H), 9.09 (s, 1H) MS m/z 407 (M+1)+

Example 5

3-(1-ethyl-1H-imidazo[4,5-c]pyridin-2-yl)-5-(4-fluorophenyl)pyrazin-2-amine

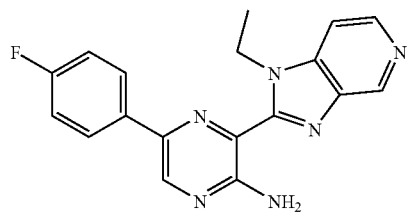

The title compound was synthesized using the procedure recited in Example 3, except 4-fluorophenylboronic acid was utilized.

1H NMR (400 MHz, DMSO-D6) δ ppm 1.48 (t, J=7.42 Hz, 3H), 4.94 (q, J=7.69 Hz, 2H), 7.35 (m, 2H), 7.81 (d, J=5.63 Hz, 1H), 8.04 (m, 2H), 8.45 (d, J=5.63 Hz, 1H) 8.80 (s, 1H) 9.09 (s, 1H)

Example 6

3-(1-ethyl-1H-imidazo[4,5-c]pyridin-2-yl)-5-thien-2-ylpyrazin-2-amine

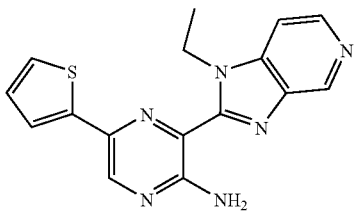

The title compound was synthesized using the procedure recited in Example 3, except 2-thiopheneboronic acid was utilized.

1H NMR (400 MHz, DMSO-D6) δ ppm 1.51 (t, J=6.96 Hz, 3H), 4.98 (q, J=7.14 Hz, 2H), 7.19 (dd, J=4.94 3.48 Hz, 1H), 7.61 (dd, J=6.04 1.10 Hz, 1H) 7.76 (dd, J=3.66 1.10 Hz, 1H) 7.82 (dd, J=5.49 0.73 Hz, 1H), 8.47 (d, J=5.49 Hz, 1H), 8.84 (s, 1H) 9.10 (br, 1H) MS m/z 323 (M+1)⁺.

Example 7

5-(4-aminophenyl)-3-(1-ethyl-1H-imidazo[4,5-c]pyridin-2-yl)pyrazin-2-amine

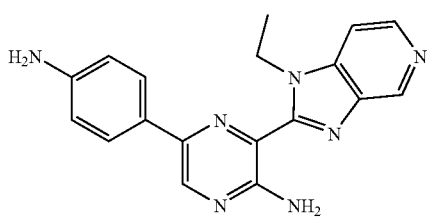

The title compound was synthesized using the procedure recited in Example 3, except 4-aminophenylboronic acid was utilized.

1H NMR (400 MHz, DMSO-D6) δ ppm 1.09 (t, J=6.96 Hz, 3H) 3.39 (q, J=7.14 Hz, 2H) 5.36 (br, 2H) 6.68 (d, J=8.61 Hz, 2H) 7.69 (d, J=8.61 Hz, 2H) 7.80 (d, J=5.68 Hz, 1H) 8.0 (br, 2H), 8.45 (d, J=5.68 Hz, 1H) 8.65 (s, 1H) 9.08 (s, 1H) MS m/z 332 (M+1)⁺.

Example 8

3-(1-ethyl-1H-imidazo[4,5-c]pyridin-2-yl)-5-pyridin-3-ylpyrazin-2-amine

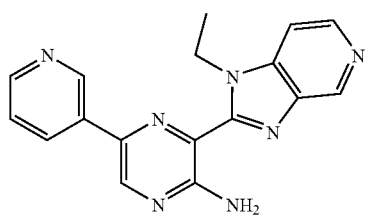

The title compound was synthesized using the procedure recited in Example 3, except pyridine-3-boronic acid was utilized.

1H NMR (400 MHz, DMSO-D6) δ ppm 1.50 (t, J=6.96 Hz, 3H) 4.96 (q, J=7.14 Hz, 2H) 7.56 (ddd, J=8.06 4.76 0.92 Hz, 1H) 7.83 (dd, J=5.68 1.10 Hz, 1H) 8.36 (m, 1H), 8.45 (d, J=5.68 Hz, 1H), 8.61 (dd, J=4.58 1.46 Hz, 1H) 8.90 (s, 1H), 9.11 (d, J=0.92 Hz, 1H) 9.23 (dd, J=2.20 0.73 Hz, 1H) MS m/z 318 (M+1)⁺.

Example 9

3-(1-ethyl-1H-imidazo[4,5-c]pyridin-2-yl)-5-(1H-indol-5-yl)pyrazin-2-amine

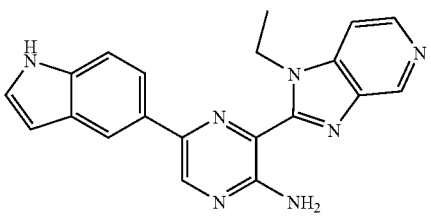

The title compound was synthesized using the procedure recited in Example 3, except 5-indolyl boronic acid was utilized.

1H NMR (400 MHz, DMSO-D6) δ ppm 1.54 (t, J=7.14 Hz, 3H) 5.03 (q, J=6.77 Hz, 2H) 6.53 (s, 1H), 7.41 (m, 1H) 7.54 (d, J=6.59 Hz, 1H), 7.77 (d, J=8.42 Hz, 1H) 7.83 (d, J=5.86 Hz, 1H) 8.10 (br, 2H), 8.19 (s, 1H), 8.47 (d, J=5.68 Hz, 1H), 8.82 (s, 1H), 9.10 (s, 1H), 11.22 (br, 1H) MS m/z 356 (M+1)⁺.

Example 10

3-[1-(2-methoxyethyl)-1H-benzimidazol-2-yl]-5-thien-2-ylpyrazin-2-amine

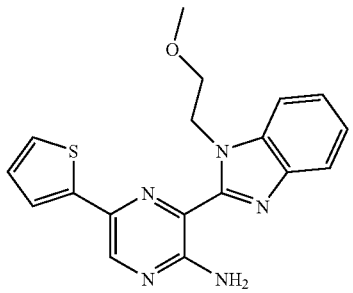

(a) Preparation of 3-(1H-benzimidazol-2-yl)pyrazin-2-amine

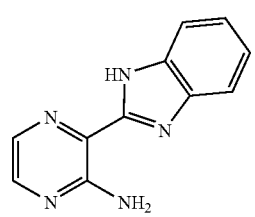

The title compound was synthesized using the procedure recited in example 1 (d), except o-phenylene diamine was utilized.

1H NMR (400 MHz, DMSO-D6) δ ppm 7.24 (m, 2H), 7.53 (d, J=6.73 Hz, 1H), 7.73 (d, J=7.01 Hz, 1H) 7.95 (d, J=2.47 Hz, 1H), 8.14 (d, J=2.47 Hz, 1H) 13.12 (br, 1H)

(b) Preparation of 3-[1-(methoxyethyl)-1H-benzimidazol-2-yl]pyrazin-2-amine

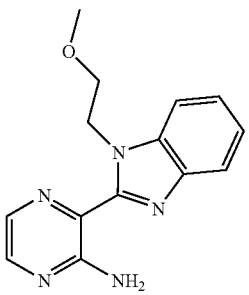

3-(1H-benzimidazol-2-yl)pyrazin-2-amine (0.302 g, 0.14 mmol) was dissolved in N,N-dimethyl formamide (10 mL) and treated with 2-bromoethyl methyl ether (0.15 mL, 0.16 mmol) and cesium carbonate (0.475 g, 1.4 mmol). The mixture was stirred at ambient temperature for 20 hours and then filtered through celite. The filtrate was concentrated and partitioned between ethyl acetate and water. The mixture was extracted into ethyl acetate (×3) and the combined organic layers were washed with water, and then with saturated sodium chloride. The organics were dried over magnesium sulfate, filtered and concentrated. Trituration with diethyl ether afforded the title compound as tan solids (0.275 g, 0.10 mmol).

1H NMR (400 MHz, DMSO-D6) δ ppm 3.17 (s, 3H) 3.74 (t, J=5.49 Hz, 2H), 4.98 (t, J=5.49 Hz, 2H), 7.33 (m, 2H), 7.69 (d, J=8.06 Hz, 1H) 7.77 (d, J=8.79 Hz, 1H) 7.97 (d, J=2.38 Hz, 1H), 8.13 (d, J=2.38 Hz, 1H). MS m/z 270 (M+1)+.

(c) Preparation of 5-bromo-3-[1-(methoxyethyl)-1H-benzimidazol-2-yl]pyrazin-2-amine

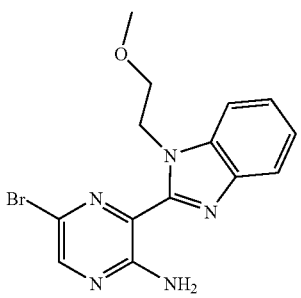

The title compound was synthesized using the procedure recited in Example 2.

1H NMR (400 MHz, DMSO-D6) δ ppm 3.21 (s, 3H), 3.78 (t, J=5.86 Hz, 2H), 4.90 (t, J=5.86 Hz, 2H), 7.35 (m, 2H), 7.70 (d, J=8.42 Hz, 1H) 7.78 (d, J=7.69 Hz, 1H), 8.26 (s, 1H) MS m/z 347/349 (M+1)+.

(d) Preparation of 3-[1-(2-methoxyethyl)-1H-benzimidazol-2-yl]-5-thien-2-ylpyrazin-2-amine

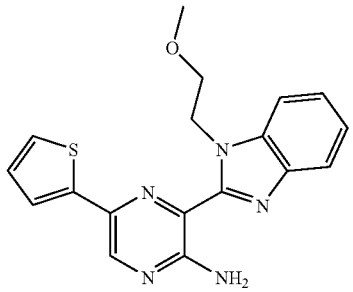

The title compound was synthesized using the procedure recited in Example 3, except 2-thiopheneboronic acid was utilized.

1H NMR (400 MHz, DMSO-D6) δ ppm 3.17 (s, 3H), 3.87 (d, J=5.13 Hz, 2H), 5.11 (d, J=5.13 Hz, 2H) 7.18 (m, 1H), 7.34 (m, 2H) 7.59 (dd, J=5.13 1.10 Hz, 1H) 7.73 (m, 2H) 7.78 (d, J=7.69 Hz, 1H) 8.76 (s, 1H) MS m/z 352 (M+1)+.

Example 11

3-(1H-benzimidazol-2-yl)-5-(3-fluorophenyl)pyrazin-2-amine

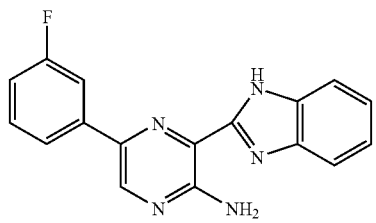

(a) Preparation of Methyl 3-amino-6-bromopyrazine-2-carboxylate

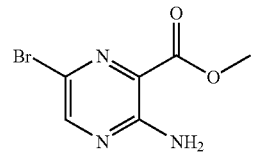

Methyl 2-aminopyrazine-3-carboxylate (5.0 g, 32.65 mmol) was dissolved in 100 mL of THF and treated with N-Bromosuccinimide (6.9 g, 39.18 mmol) all at once. The mixture was stirred at room temperature for 1.5 hrs, and then another 0.5 equivalents of N-bromosuccinimide was added and stirring continued for 1 hr. 10 grams of sodium sulfate were added, the mixture was vigorously stirred for 15 minutes, and the solvent was removed in vacuo. The residue obtained was suspended in 250 mL of water and stirred rapidly. Filtration afforded the title compound, methyl 3-amino-6-bromopyrazine-2-carboxylate, as a tan solid (6.33 g).

1H NMR (300 MHz, DMSO-D6) δ ppm 3.84 (s, 3H), 7.54 (bs, 2H), 8.41 (s, 1H) MS m/z 232, 234 (M+1)+ bromine isotopes (b) Preparation of 3-amino-6-(3-fluorophenyl)pyrazine-2-carboxylic acid

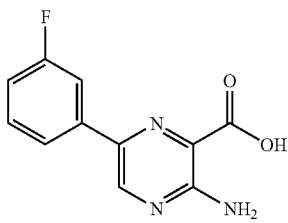

Methyl 3-amino-6-bromopyrazine-2-carboxylate (0.116 g, 0.5 mmol), 3-fluorophenylboronic acid (0.14 g, 1.0 mmol), dichlorobis(triphenylphosphine)palladium(II) (0.018 g, 0.02 mmol), and K$_2$CO$_3$ (0.14 g, 1.0 mmol) were combined in 3 mL of 4:1 CH$_3$CN:H$_2$O and heated to 150° C. for 10 minutes in the SmithSynthesizer microwave. Upon cooling, the reaction mixture was diluted with MeOH and H2O to dissolve all but the catalyst. The mixture was filtered and the pH was adjusted to 6 with 2N HCl. The solution was concentrated in vacuo, and the solids were collected to afford 3-amino-6-(3-fluorophenyl)pyrazine-2-carboxylic acid (96 mg) as a yellow solid.

1H NMR (400 MHz, DMSO-D6) δ ppm 7.20 (m, 1H), 7.50 (td, J=8.06, 6.23 Hz, 1H), 7.59 (s, 2H), 7.94 (d, J=7.87 Hz, 1H), 7.98 (m, 1H), 8.95 (s, 1H), 13.02 (s, 1H) MS m/z 234 (M+1)+.

(c) Preparation of 3-(1H-benzimidazol-2-yl)-5-(3-fluorophenyl)pyrazin-2-amine

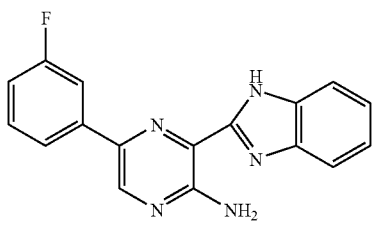

3-amino-6-(3-fluorophenyl)pyrazine-2 carboxylic acid (0.096 g, 0.41 mmol), ortho-phenylenediamine (0.049 g, 0.45 mmol), diethyl cyanophosphonate (0.07 g, 0.45 mmol), and triethylamine (0.083 g, 0.82 mmol) were combined in 5 mL of dimethoxyethane. The mixture was heated to 200° C. for 10 min in the SmithSynthesizer microwave. The cooled mixture was poured into 30 mL of H2O and the mixture was filtered to collect 3-(1H-benzimidazol-2-yl)-5-(3-fluorophenyl)pyrazin-2-amine (23 mg) as a yellow solid.

1H NMR (400 MHz, DMSO-D6) δ ppm 7.26 (m, 3H), 8.85 (s, 1H), 8.23 (m, 1H), 8.08 (d, J=8.24 Hz, 1H), 8.0-7.4 (bs, 2H), 7.77 (d, J=8.06 Hz, 1H), 7.64 (d, J=7.87 Hz, 1H), 7.52 (td, J=8.01, 6.32 Hz, 1H), 13.08 (s, 1H), MS m/z 306 (M+1)+.

Example 12

3-(1H-benzimidazol-2-yl)-5-(4-fluorophenyl)pyrazin-2-amine

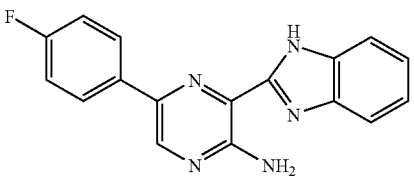

(a) Preparation of 3-amino-6-(4-fluorophenyl)pyrazine-2-carboxylic acid

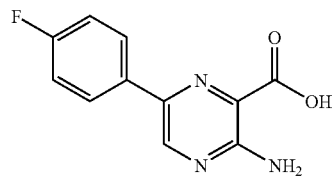

The title compound was synthesized using the procedure recited in example 11b, except 4-fluorophenylboronic acid was utilized.

1H NMR (300 MHz, DMSO-D6) δ ppm 7.28 (t, J=9.00 Hz, 2H), 7.48 (bs, 2H), 8.12 (m, 2H) 8.88 (s, 1H), 13.00 (s, 1H) MS m/z 234 (M+1)+

(a) Preparation of 3-(1H-benzimidazol-2-yl)-5-(4-fluorophenyl)pyrazin-2-amine

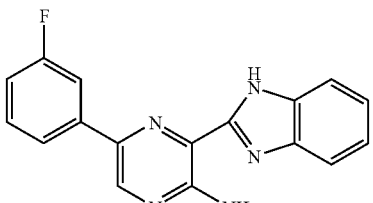

The title compound was synthesized using the procedure recited in example 11c.

1H NMR (300 MHz, DMSO-D6) δ ppm 7.31 (m, 6H), 7.64 (d, J=8.11 Hz, 1H), 7.77 (d, J=8.11 Hz, 1H), 8.33 (dd, J=8.79, 5.50 Hz, 2H), 8.79 (s, 1H), 13.04 (s, 1H) MS m/z 306 (M+1)+

Example 13

4-[5-amino-6-(1-ethyl-1-H-imidazo[4,5-c]pyridin-2-yl)pyrazin-2-yl]-N,N-dimethylbenzenesulfonamide

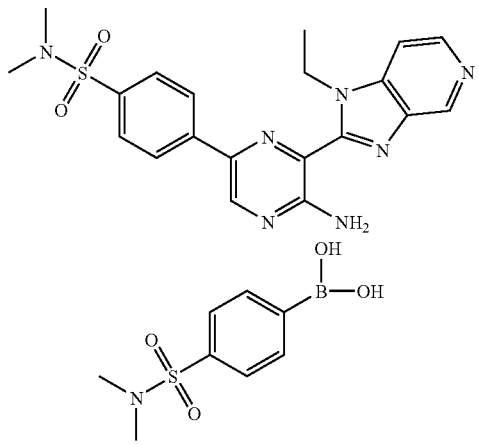

a) Preparation of 4-dimethylaminosulphonylphenylboronic acid

N,N-dimethyl-4-bromobenzenesulfonamide (8.0 g, 30.3 mmol) was dissolved in dry tetrahydrofuran (40 mL) and stirred at −70° C. under a nitrogen atmosphere. n-Butyl-lithium (1.6 M in hexanes, 19 mL, 30.4 mmol) was carefully added keeping temp. <−65° C. and the mixture stirred for 30 min. The reaction mixture was transferred by cannula to a solution of tri-isopropylborate (14 mL, 60.7 mmol) in dry tetrahydrofuran (40 mL) stirring at −70° C. under a nitrogen blanket for an hour. The mixture was warmed to room temperature over a further hour. 2M hydrochloric acid (50 mL) was added and the mixture stirred for 80 min. The aqueous layer was extracted with ethyl acetate and the organic layers combined washed with brine and dried over sodium sulfate. Concentration in vacuo gave an oily semi-solid (7.9 g). The crude product was re-crystallised from ethylacetate/cyclohexane and collected by vacuum filtration to afford 2.5 g of 4-dimethylaminosulphonylphenylboronic acid.

1H NMR (400 MHz, DMSO-D6) ppm 2.59 (s, 6H) 7.70 (d, J=8.28 Hz, 2H) 8.01 (d, J=8.28 Hz, 2H) 8.39 (s, 2H) MS m/z 230 (M+1)$^+$.

b) Syntheis of 4-[5-amino-6-(1-ethyl-1-H-imidazo[4,5-c]pyridin-2-yl)pyrazin-2-yl]-N,N-dimethylbenzenesulfonamide 5-bromo-3-(1-ethyl-1H-imidazo[4,5-c]pyridin-2-yl)pyrazin-2-amine (0.032 g, 0.10 mmol) (made in example 2), 4-dimethylaminosulphonylphenylboronic acid (0.046 g, 0.20 mmol), Pd(PPh$_3$)$_2$Cl$_2$ (0.0035 g, 0.005 mmol) and K$_2$CO$_3$ (0.050 g, 0.36 mmol) were combined in 0.5 mL of N,N-dimethylformamide and heated to 200° C. in the SmithSynthesizer microwave for 8 minutes and then for a further 8 minutes at 250° C. The reaction mixture was concentrated in vacuo and the residue purified by HPLC to give 0.0079 g of the title compound.

1H NMR (400 MHz, DMSO-D6) δ ppm 1.53 (t, J=7.03 Hz, 3H) 2.66 (s, 6H) 4.97 (q, J=6.95 Hz, 2H) 7.88 (m, 3H) 8.27 (d, J=8.28 Hz, 2H) 8.48 (d, J=5.77 Hz, 1H) 8.96 (s, 1H) 9.13 (s, 1H) MS m/z 424 (M+1)$^+$.

Example 14

3-(1-ethyl-1-H-imidazo[4,5-c]pyridin-2-yl)-5-[3-(methylsulfonyl)phenyl]pyrazin-2-amine

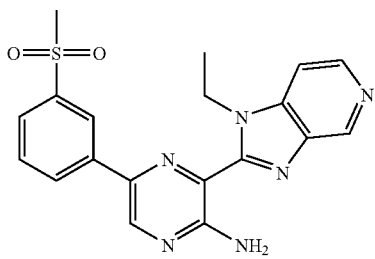

5-bromo-3-(1-ethyl-1H-imidazo[4,5-c]pyridin-2-yl)pyrazin-2-amine (0.032 g, 0.10 mmol) (made in example 2), 3-(methylsulfonyl)phenylboronic acid (0.040 g, 0.20 mmol), Pd(PPh$_3$)$_2$Cl$_2$ (0.0035 g, 0.005 mmol) and K$_2$CO$_3$ (0.050 g, 0.36 mmol) were combined in 0.5 mL of N,N-dimethylformamide and heated to 200° C. in the SmithSynthesizer microwave for 8 minutes. The reaction mixture was concentrated in vacuo and the residue purified by mass directed HPLC to give 0.0012 g of the title compound. MS m/z 395 (M+1)$^+$.

Example 15

3-{4-[5-amino-6-(1-ethyl-1-H-imidazo[4,5-c]pyridin-2-yl)pyrazin-2-yl]phenyl}propanoic acid

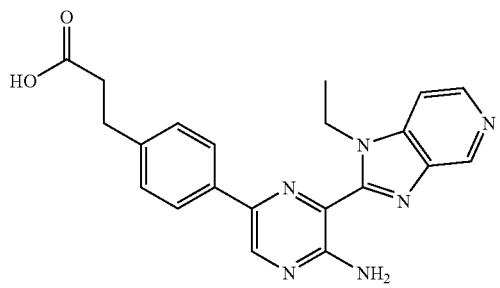

5-bromo-3-(1-ethyl-1H-imidazo[4,5-c]pyridin-2-yl)pyrazin-2-amine (0.032 g, 0.10 mmol) (made ni example 2), 4-(2-carboxyethyl)benzeneboronic acid (0.039 g, 0.20 mmol), Pd(PPh$_3$)$_2$Cl$_2$ (0.0035 g, 0.005 mmol) and K$_2$CO$_3$ (0.050 g, 0.36 mmol) were combined in 0.5 mL of N,N-dimethylformamide and heated to 200° C. in the SmithSynthesizer microwave for 8 minutes. The reaction mixture was concentrated in vacuo and the residue purified by HPLC to give 0.0084 g of the title compound.

1H NMR (400 MHz, DMSO-D6) δ ppm 1.49 (t, J=6.91 Hz, 3H) 2.59 (t, J=7.53 Hz, 2H) 2.88 (t, J=7.53 Hz, 2H) 4.97 (q, J=6.28 Hz, 2H) 7.38 (d, J=8.03 Hz, 2H) 7.81 (d, J=5.52 Hz, 1H) 7.92 (d, J=8.03 Hz, 2H) 8-8.4 (bs, 2H) 8.46 (d, J=5.52 Hz, 1H) 8.8 (s, 1H) 9.1 (s, 1H) 12-12.3 (bs, 1H) MS m/z 389 (M+1)$^+$.

Example 16

{4-[5-amino-6-(1-ethyl-1-H-imidazo[4,5-c]pyridin-2-yl)pyrazin-2-yl]phenoxy}acetic acid

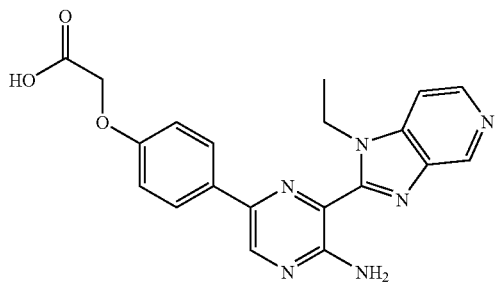

a) Synthesis of tert-butyl(4-bromophenoxy)acetate

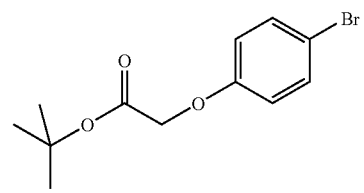

4-Bromophenol (20.4 g, 118 mmol) dissolved in dry N,N-dimethylformamide was carefully treated with sodium hydride (4 g, 167 mmol). t-Butylbromoacetate (23 g, 118 mmol) was added and the mixture heated to 75° C. for 90 minutes. The reaction was concentrated in vacuo and the residue partitioned between ethyl acetate and water. The organic phase was washed with saturated ammonium acetate and concentrated in vacuo to yield 28.1 g of tert-butyl(4-bromophenoxy)acetate.

1H NMR (400 MHz, CDCl$_3$) δ ppm 1.47 (s, 9H) 4.47 (s, 2H) 6.78 (d, J=9.04 Hz, 2H) 7.37 (d, J=9.04 Hz, 2H).

b) Synthesis of tert-butyl[4-(4,4,5,5-tetramethyl-1,3,2-dioxaboralan-2-yl)phenoxy]acetate

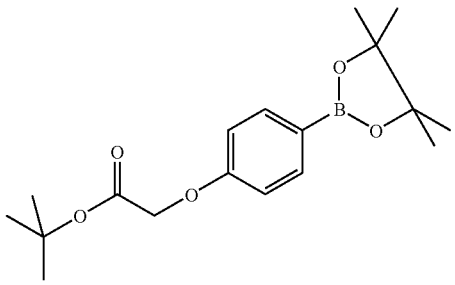

tert-Butyl(4-bromophenoxy)acetate (4.3 g, 15 mmol), potassium acetate (2.94 g, 30 mmol), PdCl$_2$ (dppf)$_2$ (167 mg, 1.5 mmol) and pinacol di-borane (3.81 g, 15 mmol) were combined in dry N,N-dimethylformamide and heated to 80° C. for 90 minutes. Concentration in vacuo followed by silica SPE chromatography afforded tert-butyl[4(4,4,5,5-tetramethyl-1,3,2-dioxaboralan-2-yl)phenoxy]acetate (4.62 g).

1H NMR (400 MHz, MeOH-D4) δ ppm 1.32 (s, 12H), 1.48 (s, 9H) 4.6 (s, 2H) 6.88 (d, J=8.53 Hz, 2H) 7.67 (d, J=8.53 Hz, 2H).

c) Synthesis of {4-[5-amino-6-(1-ethyl-1-H-imidazo[4,5-c]pyridin-2-yl)pyrazin-2-yl]phenoxy}acetic acid 5-bromo-3-(1-ethyl-1H-imidazo[4,5-c]pyridin-2-yl)pyrazin-2-amine (0.032 g, 0.10 mmol) (made in example 2), tert-butyl[4,4,5,5-tetramethyl-1,3,2-dioxaboralan-2-yl)phenoxy]acetate (0.067 g, 0.20 mmol), Pd(PPh$_3$)$_2$Cl$_2$ (0.0035 g, 0.005 mmol) and K$_2$CO$_3$ (0.050 g, 0.36 mmol) were combined in 0.5 mL of N,N-dimethylformamide and heated to 200° C. in the SmithSynthesizer microwave for 8 minutes and then for a further 8 minutes at 250° C. The reaction mixture was concentrated in vacuo and the residue purified by mass directed HPLC to give 0.0038 g of the title compound.

1H NMR (400 MHz, DMSO-D6) δ ppm 1.49 (t, J=7.03 Hz, 3H) 4.69 (s, 2H) 4.96 (q, J=6.95 Hz, 2H) 7.04 (d, J=8.78 Hz, 2H) 7.81 (d, J=5.52 Hz, 1H) 7.93 (d, J=8.78 Hz, 2H) 8-8.3 (bs, 2H) 8.45 (d, J=5.52 Hz, 1H) 8.75 (s, 1H) 9.08 (s, 1H) MS m/z 391 (M+1)$^+$.

Example 17

{3-[5-amino-6-(1-ethyl-1-H-imidazo[4,5-c]pyridin-2-yl)pyrazin-2-yl]phenoxy}acetic acid

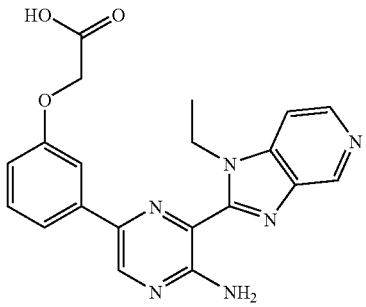

a) Synthesis of tert-butyl(3-bromophenoxy)acetate

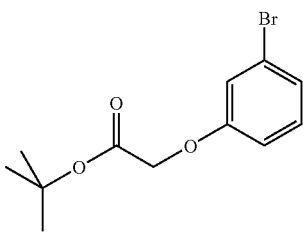

3-Bromophenol (20.4 g, 118 mmol) dissolved in dry N,N-dimethylformamide was carefully treated with sodium hydride (4 g, 167 mmol). t-Butylbromoacetate (23 g, 118 mmol) was added and the mixture heated to 75° C. for 90 minutes. The reaction was concentrated in vacuo and the residue partitioned between ethyl acetate and water. The organic phase was washed with saturated ammonium acetate and concentrated in vacuo to yield 28.9 g of tert-butyl(3-bromophenoxy)acetate.

1H NMR (400 MHz, CDCl$_3$) δ ppm 1.48 (s, 9H) 4.49 (s, 2H) 6.83 (m, 1H) 7.04 (t, J=2.01 Hz, 1H) 7.11 (d, J=1.51, 1H) 7.12 (s, 1H) MS rt=3.55 minutes b) Synthesis of tert-butyl[3-(4,4,5,5-tetramethyl-1,3,2-dioxaboralan-2-yl)phenoxy]acetate

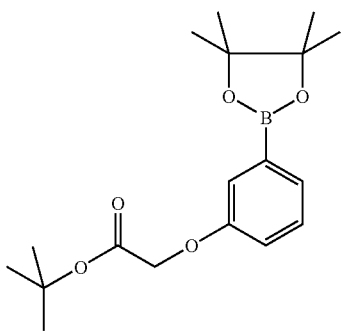

tert-Butyl(4-bromophenoxy)acetate (4.3 g, 15 mmol), potassium acetate (2.94 g, 30 mmol), PdCl$_2$(dppf)$_2$ (167 mg, 1.5 mmol) and pinacol di-borane (3.81 g, 15 mmol) were combined in dry N,N-dimethylformamide and heated to 80° C. for 90 minutes. Concentration in vacuo followed by silica SPE chromatography afforded tert-butyl[3-(4,4,5,5-tetramethyl-1,3,2-dioxaboralan-2-yl)phenoxy]acetate (3.83 g).

1H NMR (400 MHz, CDCl$_3$) δ ppm 1.33 (s, 12H) 1.48 (s, 9H) 4.56 (s, 2H) 7.02 (ddd, J=1.00, 3.01, 8.03, Hz, 1H) 7.23 (d, J=3.0 Hz, 1H) 7.28 (t, J=7.8 Hz, 1H) 7.35 (d, J=6.02 Hz, 1H).

c) Synthesis of synthesis of {3-[5-amino-6-(1-ethyl-1-H-imidazo[4,5-c]pyridin-2-yl)pyrazin-2-yl]phenoxy}acetic acid 5-bromo-3-(1-ethyl-1H-imidazo[4,5-c]pyridin-2-yl)pyrazin-2-amine (0.032 g, 0.10 mmol) (made in example 2), tert-butyl[3-(4,4,5,5-tetramethyl-1,3,2-dioxaboralan-2-yl)phenoxy]acetate (0.067 g, 0.20 mmol), Pd(PPh$_3$)$_2$Cl$_2$ (0.0035 g, 0.005 mmol) and K$_2$CO$_3$ (0.050 g, 0.36 mmol) were combined in 0.5 mL of N,N-dimethylformamide and heated to 200° C. in the SmithSynthesizer microwave for 8 minutes and then for a further 8 minutes at 250° C. The reaction mixture was concentrated in vacuo and the residue purified by mass directed HPLC to give 0.0048 g of the title compound.

1H NMR (400 MHz, DMSO-D6) δ ppm 1.49 (t, J=7.03 Hz, 3H) 4.77 (s, 2H) 4.98 (q, J=7.03 Hz, 2H) 6.95 (dd, J=8.03, 2.01 Hz, 1H) 7.42 (t, J=7.91 Hz, 1H) 7.52 (s, 1H) 7.61 (d, J=7.53, 1H) 7.8 (d, J=5.77 Hz, 1H) 8.1-8.5 (bs, 2H) 8.46 (d, J=5.52 Hz, 1H) 8.83 (s, 1H) 9.09 (s, 1H) MS m/z 391 (M+1)$^+$.

Example 18

N-{4-[5-amino-6-(1-ethyl-1-H-imidazo[4,5-c]pyridin-2-yl)pyrazin-2-yl]phenyl}methanesulfonamide

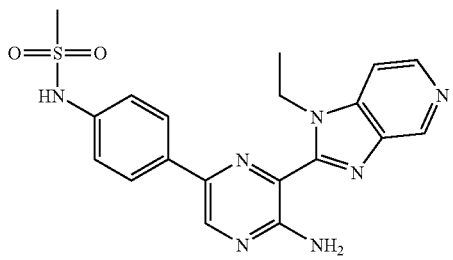

5-bromo-3-(1-ethyl-1H-imidazo[4,5-c]pyridin-2-yl)pyrazin-2-amine (0.032 g, 0.10 mmol) (made in example 2),4-(methylsulfonyl)phenylboronic acid (0.043 g, 0.20 mmol), Pd(PPh$_3$)$_2$Cl$_2$ (0.0035 g, 0.005 mmol) and K$_2$CO$_3$ (0.050 g, 0.36 mmol) were combined in 0.5 mL of N,N-dimethylformamide and heated to 200° C. in the SmithSynthesizer microwave for 8 minutes. The reaction mixture was concentrated in vacuo and the residue purified by mass directed HPLC to give 0.0014 g of the title compound.

1H NMR (400 MHz, DMSO-D6) δ ppm 1.5 (t, J=7.03 Hz, 3H) 3.05 (s, 3H) 4.96 (q, J=7.03 Hz, 2H), 7.35 (d, J=8.78 Hz, 2H) 7.82 (d, J=5.77 Hz, 1H) 7.98 (d, J=8.78 Hz, 2H) 8.1-8.4 (bs, 2H) 8.46 (d, J=5.52 Hz, 1H) 8.79 (s, 1H) 9.10 (s, 1H) 9.93 (s, 1H) MS m/z410 (M+1)$^+$.

Example 19

Benzyl 4-[5-amino-6-(1-ethyl-1-H-imidazo[4,5-c]pyridin-2-yl)pyrazin-2-yl]benzoate

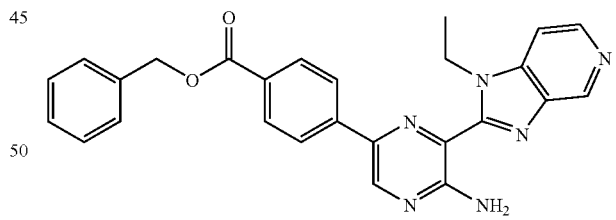

5-bromo-3-(1-ethyl-1H-imidazo[4,5-c]pyridin-2-yl)pyrazin-2-amine (0.032 g, 0.10 mmol) (made in example 2), 4-[(benzyloxy)carbonyl]phenylboronic acid (0.051 g, 0.20 mmol), Pd(PPh$_3$)$_2$Cl$_2$ (0.0035 g, 0.005 mmol) and K$_2$CO$_3$ (0.050 g, 0.36 mmol) were combined in 0.5 mL of N,N-dimethylformamide and heated to 200° C. in the SmithSynthesizer microwave for 8 minutes. The reaction mixture was concentrated in vacuo and the residue purified by mass directed HPLC to give 0.0038 g of the title compound.

1H NMR (400 MHz, DMSO-D6) δ ppm 1.51 (t, J=7.03 Hz, 3H) 4.97 (q, J=6.9 Hz, 2H), 5.38 (s, 2H) 7.38 (d, J=7.03 Hz, 1H) 7.43 (t, J=7.2 Hz, 2H) 7.51 (d, J=7.03 Hz, 2H) 7.9 (d, J=5.52 Hz, 2H) 8.14 (dd, J=8.53, 8.78 Hz, 4H) 8.5 (d, J=5.27 Hz, 1H) 8.93 (s, 1H) 9.15 (s, 1H) MS m/z 451 (M+1)⁺.

Example 20

5-[4-(benzyloxy)phenyl]-3-(1-ethyl-1-H-imidazo[4,5-c]pyridin-2-yl)pyrazin-2-amine

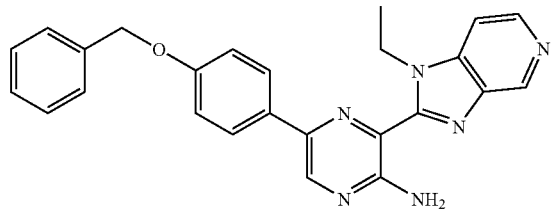

5-bromo-3-(1-ethyl-1H-imidazo[4,5-c]pyridin-2-yl)pyrazin-2-amine (0.032 g, 0.10 mmol) (made in example 2), 4-benzyloxy-phenylboronic acid (0.046 g, 0.20 mmol), Pd(PPh₃)₂Cl₂ (0.0035 g, 0.005 mmol) and K₂CO₃ (0.050 g, 0.36 mmol) were combined in 0.5 mL of N,N-dimethylformamide and heated to 200° C. in the SmithSynthesizer microwave for 8 minutes. The reaction mixture was concentrated in vacuo and the residue purified by HPLC to give 0.0099 g of the title compound.

1H NMR (400 MHz, DMSO-D6) δ ppm 1.51 (t, J=6.9 Hz, 3H) 5.0 (q, J=6.8 Hz, 2H), 5.19(s, 2H) 7.17 (d, J=8.78 Hz, 2H) 7.35 (d, J=7.28 Hz, 1H) 7.41 (t, J=7.28 Hz, 2H) 7.48 (d, J=7.28 Hz, 2H) 7.95 (d, J=8.78 Hz, 2H) 8.0 (s, 1H) 8.0-8.3 (bs, 2H) 8.55 (d, J=3.5 Hz, 1H) 8.8 (s, 1H) 9.23 (s, 1H) MS m/z 423 (M+1)⁺.

Example 21

5-[1,1'-biphenyl-3-yl)-3-(1-ethyl-1-H-imidazo[4,5-c]pyridin-2-yl)pyrazin-2-amine

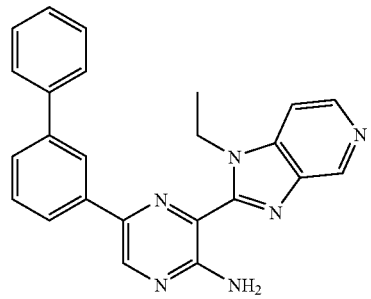

5-bromo-3-(1-ethyl-1H-imidazo[4,5-c]pyridin-2-yl)pyrazin-2-amine (0.032 g, 0.10 mmol) (made in example 2), 3-phenylbenzeneboronic acid (0.040 g, 0.20 mmol), Pd(PPh₃)₂Cl₂ (0.0035 g, 0.005 mmol) and K₂CO₃ (0.050 g, 0.36 mmol) were combined in 0.5 mL of N,N-dimethylformamide and heated to 200° C. in the SmithSynthesizer microwave for 8 minutes. The reaction mixture was concentrated in vacuo and the residue purified by mass directed HPLC to give 0.0021 g of the title compound.

1H NMR (400 MHz, DMSO-D6) δ ppm 1.55 (t, J=6.91 Hz, 3H) 5.13 (q, J=6.95 Hz, 2H), 7.43 (d, J=7.53 Hz, 1H) 7.52 (d, J=7.66 Hz, 2H) 7.64 (d, J=7.53 Hz, 1H) 7.72 (d, J=7.78 Hz, 1H) 8.03 (d, J=8.03, 1H) 8.25-8.4 (bs, 2H) 8.28 (s, 1H) 8.38 (d, J=6.78 Hz, 1H) 8.74 (d, J=6.27 Hz, 1H) 9.07 (s, 1H) 9.53 (s, 1H) MS m/z 393 (M+1)⁺.

Example 22

4-[5-amino-6-(1-ethyl-1-H-imidazo[4,5-c]pyridin-2-yl)pyrazin-2-ylbenzoic acid

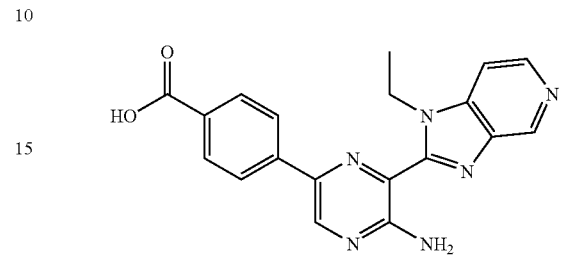

5-bromo-3-(1-ethyl-1H-imidazo[4,5-c]pyridin-2-yl)pyrazin-2-amine (0.032 g, 0.10 mmol) (made in example 2), 4-boronobenzoic acid (0.033 g, 0.20 mmol), Pd(PPh₃)₂Cl₂ (0.0035 g, 0.005 mmol) and K₂CO₃ (0.050 g, 0.36 mmol) were combined in 0.5 mL of N,N-dimethylformamide and heated to 200° C. in the SmithSynthesizer microwave for 8 minutes and then for a further 8 minutes at 250° C. The reaction mixture was concentrated in vacuo and the residue purified by mass directed HPLC to give 0.0032 g of the title compound.

1H NMR (400 MHz, DMSO-D6) δ ppm 1.51 (t, J=7.03 Hz, 3H) 4.97 (q, J=7.03 Hz, 2H), 7.84 (d, J=5.52 Hz, 1H) 8.07 (d, J=8.53 Hz, 2H) 8.13 (d, J=8.53 Hz, 2H) 8.0-8.8 (bs, 2H) 8.47 (d, J=5.52 Hz, 1H) 8.91 (s, 1H) 9.11 (s, 1H) MS m/z 361 (M+1)⁺.

Example 23 tert-butyl 3-[5-amino-6-(1-ethyl-1-H-imidazo[4,5-c]pyridin-2-yl)pyrazin-2-yl]benzylcabamate

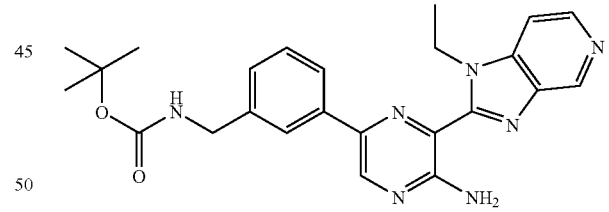

5-bromo-3-(1-ethyl-1H-imidazo[4,5-c]pyridin-2-yl)pyrazin-2-amine (0.032 g, 0.10 mmol) (made in example 2), 3-((tert-butoxycarbonyl)aminomethyl)phenylboronic acid (0.050 g, 0.20 mmol), Pd(PPh₃)₂Cl₂ (0.0035 g, 0.005 mmol) and K₂CO₃ (0.050 g, 0.36 mmol) were combined in 0.5 mL of N,N-dimethylformamide and heated to 200° C. in the SmithSynthesizer microwave for 8 minutes and then for a further 8 minutes at 250° C. The reaction mixture was concentrated in vacuo and the residue purified by HPLC to give 0.0037 g of the title compound.

1H NMR (400 MHz, DMSO-D6) δ ppm 1.40 (s, 9H) 1.53 (t, J=6.95 Hz, 3H) 4.23 (d, J=6.04 Hz, 2H) 4.98 (q, J=6.85 Hz, 2H), 6.54 (s, 1H) 7.28 (d, J=7.5 Hz, 1H) 7.47 (t, J=7.5 Hz, 2H) 7.89 (s, 1H) 7.95 (d, J=5.59 Hz, 1H) 8.28.4 (bs, 2H) 8.52 (d, J=5.67 Hz, 1H) 8.81 (s, 1H) 9.19 (s, 1H) MS m/z 446 (M+1)⁺.

Example 24

3 (1-ethyl-1H-imidazo[4,5-c]pyridin-2-yl)-5-(1H-pyrrol-2-yl)pyrazin-2-amine formate

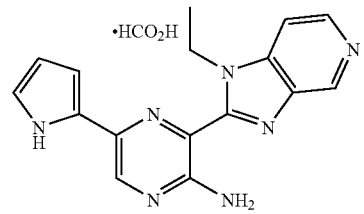

5-bromo-3-(1-ethyl-1H-imidazo[4,5-c]pyridin-2-yl)pyrazin-2-amine (0.020 g, 0.063 mmol) (made in example 2), 1-(tert-butoxycarbonyl)pyrrole-2-boronic acid (0.052 g, 0.25 mmol), Pd(PPh$_3$)$_2$Cl$_2$ (0.004 g, 0.0057 mmol) and K$_2$CO$_3$ (0.050 g, 0.25 mmol) were combined in 0.5 mL of N,N-dimethylformamide and heated to 200° C. in the SmithSynthesizer microwave for 8 minutes. The reaction mixture was concentrated in vacuo and the residue purified by HPLC to give 0.0027 g of the title compound.

1H NMR (400 MHz, DMSO-D6) δ ppm 1.42 (t, J=7.0 Hz, 3H) 4.95 (q, J=6.90 Hz, 2H), 6.18 (d, J=2.4 Hz, 1H) 6.65 (s, 1H) 6.92 (s, 1H) 7.8 (d, J=5.6 Hz, 1H) 8.0 (bs, 2 H) 8.16 (s, 1H) 8.44 (d, J=5.6 Hz, 1H) 8.60 (s, 1H) 9.07 (s, 1H) 11.19 (s, 1H) MS m/z 306 (M+1)$^+$.

Example 25

3 (1-ethyl-1H-imidazo[4,5-c]pyridin-2-yl)-5-(1H-indol-2-yl)pyrazin-2-amine formate

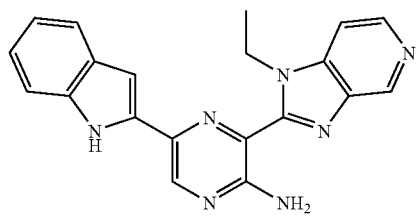

5-Bromo-3-(1-ethyl-1H-imidazo[4,5-c]pyridin-2-yl)pyrazin-2-amine (0.020 g, 0.063 mmol) (made in example 2), tert-butyl 2-borono-1H-indole-1-carboxylate (0.062 g, 0.25 mmol), Pd(PPh$_3$)$_2$Cl$_2$ (0.004 g, 0.0056 mmol) and K$_2$CO$_3$ (0.050 g, 0.25 mmol) were combined in 0.5 mL of N,N-dimethylformamide and heated to 200° C. in the SmithSynthesizer microwave for 8 minutes. The reaction mixture was concentrated in vacuo and the residue purified by HPLC to give 0.008 g of the title compound.

1H NMR (400 MHz, DMSO-D6) δ ppm 1.46 (t, J=7.0 Hz, 3H) 5.02 (q, J=7.03 Hz, 2H) 7.0 (s, 1H) 7.04 (d, J=7.53 Hz, 1H) 7.13 (t, J=7.4 Hz, 1H) 7.46 (d, J=8.03 Hz, 1H) 7.59 (d, J=7.78 Hz, 1H) 7.85 (d, J=5.52 Hz, 1H) 8.1-8.3 (bs, 2H) 8.19 (s, 1H) 8.47 (d, J=5.52 Hz, 1H) 8.83 (s, 1H) 9.10 (s, 1H) 11.43 (s, 1H) MS m/z 356 (M+1)$^+$.

Example 26

5-[(4-aminophenyl)ethynyl]-3-(1-ethyl-1H-imidazo[4,5-c]pyridin-2-yl)pyrazin-2-amine

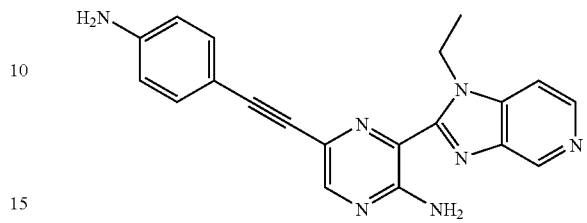

5-Bromo-3-(1-ethyl-1H-imidazo[4,5-c]pyridin-2-yl)pyrazin-2-amine (0.051 g, 0.16 mmol) (made in example 2), 4-ethynylaniline (0.060 g, 0.51 mmol), dichlorobis(triphenylphosphine)palladium(II) (0.006 g, 0.009 mmol), copper iodide (0.004 g, 0.02 mmol) and triethyl amine (3 mL) were combined and subjected to 180° C. for 1 hr in a SmithSynthesizer microwave. The resulting mixture is treated with silica gel, and the volatiles removed in vacuo. The title compound is obtained by silica gel chromatography (0.004 g).

1H NMR (400 MHz, CDCl3) δ ppm 1.56 (t, J=6.96 Hz, 3H), 3.88 (br, 2H), 4.90 (q, J=6.96 Hz, 2H), 6.66 (m, 2H), 7.40 (m, 3H), 8.29 (s, 1H), 8.50 (d, J=5.68 Hz, 1H), 9.12 (d, J=0.92 Hz, 1H). MS m/z 356 (M+1).

Biological Data

ROCK Kinase Assay:

ROCK inhibitor activity was determined using human recombinant ROCK1 kinase domain (amino acid 1-578) expressed in Sf9 cells (see WO9967283). The enzyme was purified using his-tag NTA column and Source15 HPLC chromatography. The assay of Rock-1 activity involved incubation with peptide substrate and ATP$^{33}$, the subsequent incorporation of P$^{33}$ into the peptide was quantified by Scintillation Proximity Assay (SPA—Amersham Pharmacia).

For IC50 determination, test compounds were typically dissolved at 10 mM in 100% DMSO, with subsequent serial dilution into 10% DMSO. Compounds were typically assayed over an eleven point dilution range with a concentration in the assay of 10 uM to 3 nM, in duplicate. IC50 values were calculated by bespoke curve fitting software and then converted to pIC50.

Assays were performed in clear bottomed, white walled, 96 well plates, in a total assay volume of 40 ul. The assays contained: 1 nM hROCK11; 1 uM biotinylated peptide (blotin-Ahx-AKRRRLSSLRA-CONH2); 1 uM ATP; 25 Bq per pmole ATP$^{33}$; 12.5 mM Hepes pH7.4; 7.5 mM MgCl$_2$; 0.015% BSA. The reactions were incubated at 20° C. for 120 minutes, then terminated by the addition of 10 ul of 200 mM EDTA.

Streptavidin PVT SPA beads were added to a concentration of 0.4 mg per well. The plates were shaken for 10 minutes before centrifugation at 2500 rpm for 10 minutes. P$^{33}$ incorporation was quantified by scintillation counting in a Wallac Trilux.

All exemplified Examples 1-26 were run with the recited assay and showed inhibitory activity versus Rock-1 with a pIC$_{50}$ of 5.0 or greater.

What is claimed is:

1. A compound of the Formula (I):

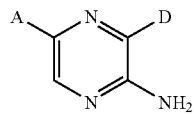 (I)

or a salt thereof wherein:

A is aryl optionally substituted with at least one $R^1$ group;

$R^1$ is $C_1$-$C_6$ alkyl, aryl, $C_1$-$C_6$ alkoxy, aryloxy, halo, —COOH, —CN, —S(O)$_2$NR$^4$R$^5$, —S(O)$_2$R, —C(O)NR$^4$R$^5$, —NRR', —N(H)C(O)NR$^4$R$^5$, —O(CH$_2$)$_n$COOH, —(CH$_2$)$_n$COOH, —C(O)O(CH$_2$)$_n$R, —(CH$_2$)$_n$N(H)C(O)OR, or —N(R')S(O)$_2$R;

R is —H, $C_1$-$C_6$ alkyl, aryl, or heteroaryl;

R' is —H or $C_1$-$C_3$ alkyl;

D is selected from the group consisting of:

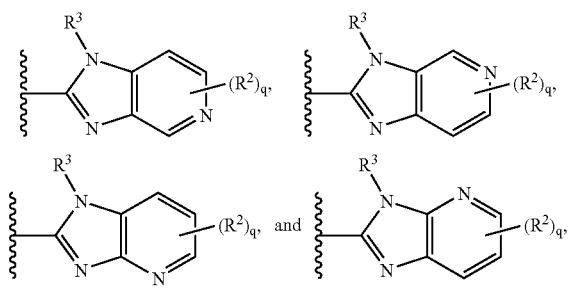

$R^2$ is —H, halo, $C_1$-$C_6$ alkyl, $C_1$-$C_6$ alkoxy, aryl, heteroaryl, —S(O)$_2$NR$^4$R$^5$, —COOH, —C(O)OR$^6$, —C(O)NR$^4$R$^5$, NRR', —N(H)C(O)NRR', —N(H)C(O)R, or —N(H)S(O)$_2$R;

q is 1, 2, 3, or 4;

$R^3$ is —H, $C_1$-$C_3$ alkyl, aryl, aralkyl, or heteroaryl;

$R^4$ is —H or $C_1$-$C_3$ alkyl;

$R^5$ is —H or $C_1$-$C_3$ alkyl; or $R^4$ and $R^5$ together with the nitrogen to which they are attached form a heterocyclyl ring, said ring optionally containing 1 or 2 additional oxygen, S(O)$_m$, or nitrogen atoms; said nitrogen atoms being optionally substituted by a $C_1$-$C_3$ alkyl group;

m is 0, 1, or 2; and $R^6$ is $C_1$-$C_6$ alkyl.

2. A pharmaceutical composition comprising a therapeutically effective amount of a compound of claim 1 and one or more of pharmaceutically acceptable carriers, diluents and excipients.

3. The compound of claim 1, wherein D is:

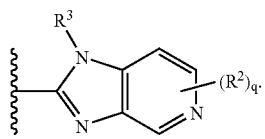

4. A compound selected from the group consisting of:

3-(1-ethyl-1H-imidazo[4,5-c]pyridin-2-yl)-5-phenylpyrazin-2-amine;

3-(1-ethyl-1H-imidazo[4,5-c]pyridin-2-yl)-5-(3,4,5-trimethoxyphenyl)pyrazin-2-amine;

3-(1-ethyl-1H-imidazo[4,5-c]pyridin-2-yl)-5-(4-fluorophenyl)pyrazin-2-amine;

5-(4-aminophenyl)-3-(1-ethyl-1H-imidazo[4,5-c]pyridin-2-yl)pyrazin-2-amine;

4-[5-amino-6-(1-ethyl-1-H-imidazo[4,5-c]pyridin-2-yl)pyrazin-2-yl]-N,N-dimethylbenzenesulfonamide;

3-(1-ethyl-1-H-imidazo[4,5-c]pyridin-2-yl)-5-[3-(methylsulfonyl)phenyl]pyrazin-2-amine;

3-{4-[5-amino-6-(1-ethyl-1-H-imidazo[4,5-c]pyridin-2-yl)pyrazin-2-yl]phenyl}propanoic acid;

{4-[5-amino-6-(1-ethyl-1-H-imidazo[4,5-c]pyridin-2-yl)pyrazin-2-yl]phenoxy}acetic acid;

{3-[5-amino-6-(1-ethyl-1-H-imidazo[4,5-c]pyridin-2-yl)pyrazin-2-yl]phenoxy}acetic acid;

N-{4-[5-amino-6-(1-ethyl-1-H-imidazo[4,5-c]pyridin-2-yl)pyrazin-2-yl]phenyl}methanesulfonamide;

benzyl 4-[5-amino-6-(1-ethyl-1-H-imidazo[4,5-c]pyridin-2-yl)pyrazin-2-yl]benzoate;

5-[4-(benzyloxy)phenyl]-3-(1-ethyl-1-H-imidazo[4,5-c]pyridin-2-yl)pyrazin-2-amine;

5-[1,1'-biphenyl-3-yl]-3-(1-ethyl-1-H-imidazo[4,5-c]pyridin-2-yl)pyrazin-2-amine;

4-[5-amino-6-(1-ethyl-1-H-imidazo[4,5-c]pyridin-2-yl)pyrazin-2-ylbenzoic acid;

tert-butyl 3-[5-amino-6-(1-ethyl-1-H-imidazo[4,5-c]pyridin-2-yl)pyrazin-2-yl]benzylcarbamate;

or a salt thereof.

* * * * *